(12) United States Patent
Medelnick et al.

(10) Patent No.: US 6,541,032 B1
(45) Date of Patent: Apr. 1, 2003

(54) USE OF FINELY DIVIDED DYE-CONTAINING POLYMERS PD AS COLOR-IMPARTING CONSTITUENT IN COSMETIC COMPOSITIONS

(75) Inventors: Monika Medelnick, Ludwigshafen (DE); Ellen Pfrommer, Hassloch (DE); Thorsten Clemens, Hochdorf-Assenheim (DE); Peter Erk, Frankenthal (DE); Arno Böhm, Mannheim (DE); Sabine Kielhorn-Bayer, Maxdorf (DE); Helmut Witteler, Beindersheim (DE); Wilma M. Dausch, Limburgerhof (DE); Horst Westenfelder, Neustadt (DE); Thomas Wünsch, Speyer (DE); Klemens Mathauer, Ludwigshafen (DE); Thorsten Habeck, Meckenheim (DE); Takahiro Ikeda, Yokkaichi (JP); Hideyuki Ichihara, Kanagawa (JP)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/677,864

(22) Filed: Oct. 3, 2000

(30) Foreign Application Priority Data

Oct. 13, 1999 (DE) .................................. 199 49 382

(51) Int. Cl.$^7$ ................................................ A61K 9/14
(52) U.S. Cl. .................... 424/484; 424/401; 424/486; 424/487; 424/70.1; 424/59; 424/63; 424/64; 514/937; 514/844
(58) Field of Search .................................. 424/401, 484, 424/486, 487, 70.1, 59, 63, 64; 514/937, 844

(56) References Cited

U.S. PATENT DOCUMENTS

| | | | |
|---|---|---|---|
| 3,836,537 A | 9/1974 | Boerwinkle et al. ........... 260/29 |
| 3,880,869 A | 4/1975 | Scheuermann et al. ...... 260/296 |
| 3,883,489 A | 5/1975 | Matschke et al. ............. 260/78 |
| 4,237,253 A | 12/1980 | Jacquet et al. ................. 526/75 |
| 4,250,289 A | 2/1981 | Denzinger et al. ........... 526/201 |
| 4,446,324 A | 5/1984 | Graser ........................... 546/37 |
| 4,481,328 A | 11/1984 | Harréus et al. .............. 524/493 |
| 4,486,587 A | 12/1984 | Seybold ........................ 544/99 |
| 4,618,694 A | 10/1986 | Iden et al. ................... 558/416 |
| 4,680,332 A | 7/1987 | Hair et al. ................... 524/377 |
| 4,814,101 A | 3/1989 | Schieferstein ............... 252/174 |
| 4,841,066 A | 6/1989 | Goertz et al. ............... 548/335 |
| 4,859,756 A | 8/1989 | Goertz et al. ............... 526/263 |
| 5,000,937 A | 3/1991 | Grollier et al. ............... 424/47 |
| 5,078,829 A | 1/1992 | Morosini .................... 156/584 |
| 5,108,654 A | 4/1992 | Ragaini ....................... 252/314 |
| 5,143,723 A * | 9/1992 | Calvo et al. ................. 424/63 |
| 5,225,478 A | 7/1993 | Beckerle et al. ............. 524/510 |
| 5,252,704 A | 10/1993 | Bright et al. ............... 528/501 |
| 5,342,897 A | 8/1994 | Franzman et al. .......... 525/221 |
| 5,462,978 A | 10/1995 | Penzel et al. ................ 523/342 |
| 5,473,013 A | 12/1995 | Zeller et al. .................. 525/57 |
| 5,607,864 A | 3/1997 | Ricciero et al. ............. 436/533 |
| 5,650,513 A | 7/1997 | Langhals et al. ............. 546/38 |
| 5,703,156 A | 12/1997 | Sauer .......................... 524/802 |
| 5,710,197 A | 1/1998 | Fischer et al. ................ 524/82 |
| 5,880,252 A | 3/1999 | Kim et al. ................... 528/332 |
| 5,897,811 A | 4/1999 | Lesko ......................... 252/301 |
| 5,962,554 A | 10/1999 | Pakusch et al. ............. 523/342 |
| 6,254,877 B1 * | 7/2001 | De La Poterie et al. .... 424/401 |

FOREIGN PATENT DOCUMENTS

| | | |
|---|---|---|
| CA | 2066226 | 3/1991 |
| DE | 22 38 903 | 2/1974 |
| DE | 44 36 892 | 1/1996 |
| DE | 195 21 500 | 6/1996 |
| EP | 51 144 | 5/1982 |
| EP | 691 390 | 1/1996 |
| GB | 1 523 475 | 8/1978 |
| GB | 1 569 637 | 6/1980 |
| GB | 2 250 930 | 6/1992 |
| JP | 59 162 161 | 9/1984 |
| WO | WO 96/22332 | 7/1996 |
| WO | WO 98/03576 | 1/1998 |
| WO | WO 98/03577 | 1/1998 |
| WO | WO 99/40123 | 8/1999 |
| WO | PCT/EP 99/40123 | 4/2000 |

OTHER PUBLICATIONS

Ullmann's Encyclopedia of Industrial Chemistry, 5th Ed. vol. A18 pp. 156–161.

Ullmann's Encylcopedia of Industrial Chemistry, 5th Ed. vol. A9 pp 313–318.

Ullmann's Encyclopedia of Industrial Chemistry, 5th Ed. vol. A2 pp. 402–403.

Ullmann's Encyclopedia of Industrial Chemistry, 5th Ed. vol. A21 pp. 169–171.

Cosmetic Legislation, vol. 1 Cosmetic products, European Commission (1999) pp. 64–66.

Nuyken " Synthesestrategien für Telechele, Makromonomere, Block–und Pfopf–copolymere" Makromolekulare Chemie vol. 223 (1994) pp. 29–46.

(List continued on next page.)

Primary Examiner—Thurman K. Page
Assistant Examiner—Todd D Ware
(74) Attorney, Agent, or Firm—Keil & Weinkauf

(57) ABSTRACT

The present invention describes the use of finely divided dye-containing polymers PD in the form of an aqueous polymer dispersion or a polymer powder obtainable therefrom, the polymer matrix of which comprises at least one organic dye D in homogeneously dispersed form, as color-imparting constituent in cosmetic compositions. The present invention also describes cosmetic compositions which comprise a color-containing polymer in an amount of from 0.1 to 50% by weight, based on the total weight of the cosmetic composition, and additives customary for cosmetic compositions.

8 Claims, No Drawings

OTHER PUBLICATIONS

Tang et al. "Miniemulsion Polymerization–A Comparative Study of Preparative Variables" Journal of Applied Polymer Science vol. 43 (1991) pp. 1059–1066.

Schrader et al. "Grundlagen und Rezepturen der Kosmetika" (1989) pp. 906–935.

Bartl et al. "Makromolekulare Stoffe" (1961) pp. 192–208.

Ullmanns Encyklopädie der technischen Chemie Band 9 pp. 313–318.

Ullmanns Encyklopädie der technischen Chemie Band 8, pp. 244–300.

Ullmanns Encyklopädie der technischen Chemie Band 7, pp. 585–647.

Ullmanns Encyklopädie der technischen Chemie Band 10, pp. 155–165.

* cited by examiner

USE OF FINELY DIVIDED DYE-CONTAINING POLYMERS PD AS COLOR-IMPARTING CONSTITUENT IN COSMETIC COMPOSITIONS

The present invention relates to the use of finely divided dye-containing polymers PD as color-imparting constituent in cosmetic compositions.

Cosmetic compositions are generally used to protect the skin, in particular facial skin, hair, fingernails and toenails from mechanical effects, from drying out and from infections. In the case of a number of cosmetic compositions the intention is for an optical effect to also be achieved in addition to the care and protecting action. Sometimes, the optical effect is even of primary importance. Examples of cosmetic compositions with which an optical effect is to be achieved are compositions for treating facial skin, such as kohl pencils, eyeliners, eye shadows, foundation formulations, tinting creams, stage make-up, hair-treatment compositions, such as wet gels, hair gels with glimmer look, styling gels, hair spray, hair mascara, and also nail varnishes and sunscreen formulations, such as sunblock creams and sunblock sticks. Cosmetics for which the optical effect is of primary importance are frequently also referred to as decorative cosmetics.

Decorative cosmetics generally comprise organic or inorganic pigments as color-imparting constituent. These are usually incorporated into the cosmetics during their preparation. Because of their insolubility, the pigments behave largely inertly toward the other constituents of the cosmetic composition, in contrasst to soluble dyes. In addition, the insolubility of the pigments has the advantage that lasting coloration of the parts of the body which have been treated with the cosmetic composition can be avoided.

A disadvantage of using pigments is that their color brilliance is lower than that of organic dyes. In addition, traditional pigments have to be digested prior to their use in cosmetic compositions in order to ensure fine distribution of the pigment within the cosmetic composition. Fine dispersion of the pigment is necessary in order to guarantee uniform coloration of the cosmetic composition and to achieve adequate depth of color even where relatively small amounts of pigment are used. To digest the pigment, the pigment is usually ground in some of the oily phase to give a pigment-containing paste, which is then rolled or milled to give the desired degree of fineness. In this connection, it is important that the color paste is not too thin so that a good grinding effect is achieved. It must, however, not be too solid either since otherwise the color paste cannot be incorporated into the cosmetic composition without lumps.

It is an object of the present invention to provide a color-imparting constituent suitable for cosmetic compositions which can be readily incorporated into the cosmetic compositions and at the same time has the advantages of pigments, namely chemically inert behavior toward the other constituents of the cosmetic composition and a low solubility in water. In addition, the color-imparting constituent should have a color brilliance which is increased compared with inorganic or organic pigments.

We have now found, surprisingly, that this object is achieved by finely divided dye-containing polymers PD, the polymer matrix of which comprises at least one organic dye D in homogeneously dispersed form. The finely divided polymers PD are used here in the form of their aqueous polymer dispersion or in the form of a polymer powder prepared therefrom.

Accordingly, the present invention relates to the use of finely divided dye-containing polymers PD in the form of an aqueous polymer dispersion or a polymer powder obtainable therefrom, the polymer matrix of which comprises at least one organic dye in homogeneously dispersed form, as color-imparting constituent in cosmetic compositions.

Homogeneous dispersion of the organic dye means that the organic dye in the polymer matrix of the dye-containing polymer is present in molecularly disperse distribution, i.e. is present in monomolecularly dissolved form or dissolved in the form of bi- or higher-molecular dye aggregates.

The term dye encompasses here and below chemical compounds or salts of chemical compounds, and charge-transfer complexes of chemical compounds having a chromophore which has an absorption maximum in the wavelength range from 400 to 850 nm and thus brings about a color impression for the human eye (conventional dyes), and which itself optionally also emits light in the visible region (fluorescent dyes). Dyes for the purposes of this invention are also compounds having an absorption maximum in the range from 250 to 400 nm which emit fluorescent radiation in the visible region upon irradiation with UV light (optical brightener). Dyes for the purposes of this invention are also chemical compounds which absorb light of wavelength <400 nm and deactivate it in a nonradiative manner (UV stabilizers resp. UV absorbers).

It is an essential feature of the invention that the dye can be homogeneously dispersed in the polymer matrix of the dye-containing polymer. This is usually ensured when the organic dye, optionally in the form of a salt, has at least limited solubility in the low molecular weight constituents which form the polymer matrix (monomers). The organic dye preferably has a solubility which is greater than the intended use amount in the polymer. Suitable dyes D have, in particular, a solubility of >0.5% by weight, in particular >1% by weight and very particularly preferably >5% by weight in the monomers.

Depending on the color intensity of the dye, the dye-containing polymer PD generally comprises at least 0.1% by weight, based on the weight of the polymer matrix, preferably 0.5 to 50% by weight, in particular 1 to 30% by weight and especially preferably 5 to 30% by weight, of at least one organic dye D.

The monomer-soluble dyes D generally do not have ionic functional groups. The dye chromophore will have one or more substituents which improve the solubility of the dyes in the nonpolar or slightly polar monomers. Suitable substituents are, for example, $C_1$–$C_{10}$-alkyl, which may optionally be interrupted by heteroatoms and/or substituted by hydroxyl and/or halogen, $C_1$–$C_{10}$-alkoxy, amino, $C_1$–$C_{10}$-alkylamino, bis-$C_1$–$C_{10}$-dialkylamino, $C_1$–$C_{10}$-alkylaminocarbonyl, $C_1$–$C_{10}$-alkyloxycarbonyl, $C_1$–$C_{10}$-alkylcarbonylamino, $C_1$–$C_{10}$-alkylcarbonyloxy, $C_6$–$C_{10}$-aryl, $C_6$–$C_{10}$-aryloxy, $C_6$–$C_{10}$-arylcarbonyl, $C_6$–$C_{10}$-arylcarbonyloxy, $C_6$–$C_{10}$-arylamino, $C_6$–$C_{10}$-arylcarbonylamino, $C_6$–$C_{10}$-aryloxycarbonyl, $C_6$–$C_{10}$-arylaminocarbonyl, $C_6$–$C_{10}$-aryl-$C_1$–$C_4$-alkyl, heterocyclyl, halogen and nitro.

$C_1$–$C_{10}$-Alkyl means here and below both linear or branched alkyl having 1 to 10 carbon atoms which may be interrupted by one or more nonadjacent oxygen atoms, sulfur atoms, imino groups or alkylimino groups, and/or may be mono- or polysubstituted by halogen or hydroxyl. Examples of unsubstituted alkyl groups include methyl, ethyl, n-propyl, isopropyl, n-butyl, 2-butyl, isobutyl, tert-butyl, n-pentyl, isopentyl, neopentyl, tert-pentyl, hexyl, 2-methylpentyl, heptyl, 1-ethylpentyl, n-octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl, eicosyl. Examples of alkyl groups interrupted by oxygen include 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-isopropoxypropyl, 2- or 3-butoxypropyl, 2- or 3-(2-ethylhexyloxypropyl) etc. Halogen-substituted alkyl groups include, in particular, perfluoroalkyl groups having 1 to 4 carbon atoms, such as trifluoromethyl. Examples of hydroxyl-substituted alkyl groups are hydroxymethyl, 1- or 2-hydroxyethyl, 1-, 2- or 3-hydroxypropyl, 1,2-bishydroxyethyl.

$C_6$–$C_{10}$-Aryl means phenyl or naphthyl which is optionally substituted by 1, 2 or 3 substituents chosen from $C_1$–$C_4$-alkyl, $C_1$–$C_4$-alkoxy, halogen, hydroxyl, which can optionally also be ethoxylated. $C_6$–$C_{10}$-Aryl-$C_1$–$C_4$-alkyl stands for $C_6$–$C_{10}$-aryl bonded by a $C_1$–$C_4$-alkylene group. Examples of $C_1$–$C_4$-alkylene include methylene, 1,1-ethylene, 1,2-ethylene, 1,1-propylene, 1,2-propylene, 2,2-propylene, 1,3-propylene and 1,4-butylene. Examples of $C_6$–$C_{10}$-aryl-$C_1$–$C_4$-alkyl include, in particular, benzyl and 2-phenylethyl which are optionally also substituted.

Examples of cycloalkyl are aliphatic monocycles such as cyclopentyl, cyclohexyl and cycloheptyl, and aliphatic polycycles such as norbornyl, adamantyl or decahydronaphthyl which, like aryl, may be substituted. Heterocycloalkyl means aliphatic mono- and polycyclic radicals which have at least one heteroatom, e.g. S, O and/or N, in the ring. Examples thereof are pyrrolidinyl, furanyl, piperidinyl, oxazolidinyl, morpholinyl and tetrahydropyranyl. Heteroaryl means radicals derived from optionally substituted or benzo-fused heteroatoms such as thiophene, pyrrole, pyrazole, imidazole, oxazole, thiazole, pyridine, pyrimidine, pyridazine, triazine, quinoline, quinazoline and the like.

Examples of monomer-soluble neutral dyes D are the compounds referred to as disperse dyes and those referred to as solvent dyes in accordance with the Colour Index, which are also referred to as dispersion dyes. A list of suitable dispersion dyes is given, for example, in Ullmanns Enzyklopadie der technischen Chemie [Ullmann's Encyclopedia of Industrial Chemistry], 4$^{th}$ edition, Vol. 10, pp. 155–165 (see also Vol. 7, p. 585ff—Anthrachinonfarbstoffe [Anthraquinone Dyes]; Vol. 8, p. 244ff—Azofarbstoffe [Azo Dyes]; Vol. 9, p. 313ff—Chinophthalonfarbstoffe [Quinophthalone Dyes]). Express reference is hereby made to this literature reference and the compounds mentioned therein.

Dispersion dyes and solvent dyes suitable according to the invention include many different classes of dyes having various chromophores, for example anthraquinone dyes, monoazo and disazo dyes, quinophthalones, methine and azamethine dyes, naphthalimide dyes, naphthoquinone dyes and nitro dyes. Examples of dispersion dyes suitable according to the invention are the dispersion dyes from the following Colour Index list:

C. I. Disperse Yellow 1, 2, 3, 4, 5, 6, 7, 8, 9, 10, 11, 11:1, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 179, 180, 181, 182, 183, 184, 184:1, 200, 201, 202, 203, 204, 205, 206, 207, 208, 209, 210, 211, 212, 213, 214, 215, 216, 217, 218, 219, 220, 221, 222, 223, 224, 225, 226, 227, 228.

C. I. Disperse Orange 1, 2, 3, 3:3, 4, 5, 6, 7, 8, 9, 10, 11, 12, 13, 14, 15, 16, 17, 18, 19, 20, 21, 22, 23, 24, 25, 25:1, 26, 27, 28, 29, 30, 31, 32, 33, 34, 35, 36, 37, 38, 39, 40, 41, 41:1, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 126, 127, 128, 129, 130, 131, 136, 137, 138, 139, 140, 141, 142, 143, 145, 146, 147, 148.

C. I. Disperse Red 1, 2, 3, 4, 5, 5:1, 6, 7, 8, 9, 10, 11, 12, 13, 14, 15, 16, 17, 18, 19, 20, 21, 22, 23, 24, 25, 26, 27, 28, 29, 30, 30:1, 31, 32, 33, 34, 35, 36, 38, 39, 40, 41, 43, 43:1, 46, 48, 50, 51, 52, 53, 54, 55, 55:1, 56, 58, 59, 60, 61, 63, 65, 66, 69, 70, 72, 73, 74, 75, 76, 77, 79, 80, 81, 82, 84, 85, 86, 86:1, 87, 88, 89, 90, 91, 92, 93, 94, 96, 97, 98, 100, 102, 103, 104, 105, 106, 107, 108, 109, 110, 111, 112, 113, 115, 116, 117, 118, 120, 121, 122, 123, 125, 126, 127, 128, 129, 130, 131, 132, 133, 134, 135, 136, 137, 138, 139, 140, 141, 142, 143, 144, 145, 146, 147, 148, 149, 150, 151, 151:1, 152, 153, 154, 155, 156, 157, 158, 159, 160, 161, 162, 163, 164, 165, 166, 167, 167:1, 168, 169, 170, 171, 172, 173, 174, 175, 176, 177, 178, 179, 180, 181, 182, 183, 184, 185, 186, 187, 188, 189, 190, 190:1, 191, 191:1, 192, 193, 194, 195, 211, 223, 273, 274, 275, 276, 277, 278, 279, 280, 281, 302:1, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 338, 339, 340, 341, 342, 343, 344, 346, 347, 348, 349.

C. I. Disperse Violet 1, 2, 3, 4, 4:1, 5, 6, 7, 8, 9, 10, 11, 12, 13, 14, 15, 16, 17, 18, 19, 20, 21, 22, 23, 24, 25, 26, 27, 28, 29, 31, 33, 34, 35, 36, 37, 38, 39, 40, 41, 42, 43, 44, 45, 46, 47, 48, 49, 50, 51, 52, 53, 54, 55, 56, 57, 58, 59, 60, 81, 86, 87, 88, 89, 91, 92, 93, 94, 95, 96, 97.

C. I. Disperse Blue 1, 1:1, 2, 3, 3:1, 4, 5, 6, 7, 7:1, 8, 9, 10, 11, 12, 13, 13:1, 14, 15, 16, 17, 18, 19, 20, 21, 22, 23, 23:1, 24, 25, 26, 27, 28, 29, 30, 31, 32, 33, 34, 35, 36, 38, 39, 40, 42, 43, 44, 45, 47, 48, 49, 51, 52, 53, 54, 55, 56, 58, 60, 60:1, 61, 62, 63, 64, 64:1, 65, 66, 68, 70, 72, 73, 75, 76, 77, 79, 80, 81, 81:1, 82, 83, 84, 85, 86, 87, 88, 89, 90, 91, 92, 93, 94, 95, 96, 97, 98, 99, 100, 101, 102, 103, 104, 105, 106, 107, 108, 109, 111, 112, 113, 114, 115, 116, 117, 118, 119, 121, 122, 123, 124, 125, 126, 127, 128, 130, 131, 132, 133, 134, 136, 137, 138, 139, 140, 141, 142, 143, 144, 145, 146, 147, 148, 149, 150, 151, 152, 153, 154, 155, 156, 158, 159, 160, 161, 162, 163, 164, 165, 165:2, 166, 167, 168, 169, 170, 171, 172, 173, 174, 175, 195, 281, 282, 283, 283:1, 284, 285, 286, 287, 288, 289, 290, 291, 292, 293, 294, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 349.

C. I. Disperse Green 1, 2, 5, 6, 9.

C. I. Disperse Brown 1, 2, 3, 4, 4:1, 5, 7, 8, 9, 10, 11, 18, 19, 20, 21.

C. I. Disperse Black 1, 3, 4, 5, 6, 7, 8, 9, 10, 11, 12, 13, 14, 15, 20, 22, 24, 25, 26, 27, 28, 29, 29:1, 30, 31, 32, 33, 34, 36.

Examples of solvent dyes suitable according to the invention are the compounds from the following Colour Index list:

C. I. Solvent Yellow 2, 3, 7, 12, 13, 14, 16, 18, 19, 21, 25, 25:1, 27, 28, 29, 30, 33, 34, 36, 42, 43, 44, 47, 56, 62, 72, 73, 77, 79, 81, 82, 83, 83:1, 88, 89, 90, 93, 94, 96, 98, 104, 107, 114, 116, 117, 124, 130, 131, 133, 135, 141, 143, 145, 146, 157, 160:1, 161, 162, 163, 167, 169, 172, 174, 175, 176, 179, 180, 181, 182, 183, 184, 185, 186, 187, 189, 190, 191.

C. I. Solvent Orange 1, 2, 3, 4, 5, 7, 11, 14, 20, 23, 25, 31A, 40:1, 41, 45, 54, 56, 58, 60, 62, 63, 70, 75, 77, 80, 81, 86, 99, 102, 103, 105, 106, 107, 108, 109, 110, 111, 112, 113.

C. I. Solvent Red 1, 2, 3, 4, 8, 16, 17, 18, 19, 23, 24, 25, 26, 27, 30, 33, 35, 41, 43, 45, 48, 49, 52, 68, 69, 72, 73, 83:1, 84:1, 89, 90, 90:1, 91, 92, 106, 109, 111, 118, 119, 122, 124, 125, 127, 130, 132, 135, 141, 143, 145, 146, 149, 150, 151, 155, 160, 161, 164, 164:1, 165, 166, 168, 169, 172, 175, 179, 180, 181, 182, 195, 196, 197, 198, 207, 208, 210, 212, 214, 215, 218, 222, 223, 225, 227, 229, 230, 233, 234, 235, 236, 238, 239, 240, 241, 242, 243, 244, 245, 247, 248.

C. I. Solvent Violet 2, 8, 9, 11, 13, 14, 21, 21:1, 26, 31, 36, 37, 38, 45, 46, 47, 48, 49, 50, 51, 55, 56, 57, 58, 59, 60, 61.

C. I. Solvent Blue 2, 3, 4, 5, 7, 18, 25, 26, 35, 36, 37, 38, 43, 44, 45, 48, 51, 58, 59, 59:1, 63, 64, 67, 68, 69, 70, 78, 79, 83, 94, 97, 98, 99, 100, 101, 102, 104, 105, 111, 112, 122, 124, 128, 129, 132, 136, 137, 138, 139, 143.

C. I. Solvent Green 1, 3, 4, 5, 7, 28, 29, 32, 33, 34, 35.

C. I. Solvent Brown 1, 3, 4, 5, 12, 20, 22, 28, 38, 41, 42, 43, 44, 52, 53, 59, 60, 61, 62, 63.

C. I. Solvent Black 3, 5, 5:2, 7, 13, 22, 22:1, 26, 27, 28, 29, 34, 35, 43, 45, 46, 48, 49, 50.

Also suitable according to the invention are monomer-soluble derivatives of naphthalene, anthracene, perylene, terylene, quaterylene, and monomer-soluble diketopyrrolopyrrole dyes, perinone dyes, coumarin dyes, isoindoline and isoindolinone dyes, porphyrin dyes, phthalocyanine and naphthalocyanine dyes.

Suitable monomer-soluble coumarin dyes are described, for example, in U.S. Pat. No. 3,880,869 and DE-A 44 24 817, to the entire contents of which reference is hereby made.

Suitable nonpolar perylene dyes are, for example, those described in U.S. Pat. No. 4,618,694, DE-A 24 51 782, U.S. Pat. No. 379,934, U.S. Pat. No. 4,446,324, EP-A 277 980, EP-A 657 436 or WO 96/22332. Further suitable nonpolar perylene dyes are given, for example, in EP-A 73 007. Reference is hereby made to the entire contents of said publications. Examples of preferred perylene dyes are the 6,12-dicyanoperylene-1,7-dicarboxylic $C_2$–$C_{10}$-alkyl esters, the bis(N-$C_1$–$C_{10}$-alkyl)perylenetetracarboxylic diimides and the corresponding N-(alkylphenyl) compounds, which are commercially available under the Lumogen®F trade names (BASF Aktiengesellschaft, Germany), e.g. Lumogen®F Red 300, Lumogen®F Yellow 083 and Lumogen®F Orange 240.

Suitable naphthalene dyes include inter alia naphthalene-1,8-dicarboxylic imides which are substituted on the imide nitrogen by unsubstituted, linear or branched $C_1$–$C_{10}$-alkyl or aryl, and which may have $C_1$–$C_6$-alkoxy substituents in the 4- and/or 5-position of the naphthalene ring.

Suitable anthracene dyes include inter alia 9,10-diphenylanthracene, 9,10-bisphenylethynylanthracene, 1,8-dichloro-9,10-bisphenylethynylanthracene. Examples of suitable anthracene dyes are given, for example, in Ullmann's Encyclopedia of Industrial Chemistry, 5th edition, Vol. A2, p. 402 f.

Suitable porphyrin dyes include, for example, tetraphenylporphyrin and octaethylporphyrin, and the zinc or nickel complexes thereof.

Examples of suitable phthalocyanine dyes are metallophthalocyanines, in particular copper phthalocyanines which, on the phenylene units of the chromophore, have solubilizing alkyl groups having, preferably, 4 to 20 carbon atoms, where the alkyl radicals may be bonded to the chromophore directly or via a functional group, for example via a sulfonamide group. Commercially available products are, for example, tetra-$C_4$–$C_{10}$-alkylphthalocyanine complexes, such as tetra-tert-butylcopper phthalocyanine or tetra-n-octylcopper phthalocyanine, and sulfonamides of mono- or polysulfonated metallophthalocyanines with $C_{10}$–$C_{20}$-alkylamines, e.g. the tetrasulfonamide of the tetrasulfonated copper phthalocyanine with stearylamine.

According to the invention the dyes D also include optical brighteners which are soluble in the polymer matrix or in the monomers which constitute the polymer matrix, i.e. are oil-soluble. Suitable optical brighteners are, for example, compounds from the classes of bisstyrylbenzenes, stilbenes, benzoxazoles, coumarins, pyrenes and naphthalenes. It is possible to use said brighteners alone or as mixtures with one another.

The abovementioned optical brighteners are generally commercially available products which are known per se. They are described, for example, in Ullmann's Encyclopedia of Industrial Chemistry, $5^{th}$ edition, Volume A18, p. 156–161, or can be obtained by the methods cited therein.

In accordance with the definition, the organic dyes also include UV ray-absorbing compounds (UV stabilizers resp. UV absorbers) which deactivate the absorbed radiation in a nonradiative manner. Such compounds are frequently used as UV adsorbers in sunscreens.

UV absorbers include derivatives of substituted cinnamates such as octyl p-methoxycinnamate, isopentyl 4-methoxycinnamate, benzophenones, such as 4-methoxy-2-hydroxybenzophenone sulfonic acid sodium salt, salicylates such as 4-isopropylbenzylsalicylate, p-aminobenzoic acid and derivatives thereof, espcially esters thereof such as ethoxilated ethyl 4-aminobenzoat, 2-ethylhexyl 4,4-dimethylaminobenzoat, esters of 4,4-diphenylbutadien-1,1-dicarboxylic acid, e.g. the bis(2-ethylhexyl)ester, 2-phenylbenzimidazol-4-sulfonic acid and salts thereof, urocanic acid, salts thereof and esters thereof, benzoxazoles, benzotriazoles such as 2-(2H-benzotriazole-2-yl)-4-methyl-6-(2-methyl-3-((1,1,3,3-tetra-methyl-1-(trimethylsilyloxy) disiloxanyl)propyl)phenol, benzylidenecamphor and its derivatives, as mentioned, for example, in DE-A 3 836 630, e.g. 3-benzylidenecamphor, 3(4'-methylbenzyliden)d-1-campher, further α-(2-oxoborn-3-yliden) toluol-4-sulfonic acid and salts thereof, N,N,N-trimethyl-4-(2-oxoborn-3-ylidenmethyl)anilinium-methosulfate, dibenzoylmethanes such as 4-tert.-butyl-4'-methoxydibenzoyl-methane, 2,4,6-triaryltriazines such as 2,4,6-tris-{N-[4-(2-ethylhex-1-yl) oxycarbonylphenyl]amino}-1,3,5-triazin, 2'-ethylhexyl 4,4'-((6-(((tert.-butyl)aminocarbonyl)-phenylamino)-1,3,5-triazine-2,4-diyl)imino)bis benzoat, ethyl 2-cyano-3,3-diphenylacrylate and 2'-ethylhexyl 2-cyano-3,3-diphenylacrylate, and 2-phenylbenzimidazole-5-sulfonic acid and salts thereof. Further useful UV absorbers can be found in Cosmetic legislation, Vol.1, Cosmetic Products, European Commission 1999, p. 64–66, to the entire content of which is reference made hereby.

Furthermore, the dye-containing polymers PD can also comprise ionic dyes D as color-imparting constituent. These dyes are not generally soluble as such in the polymer matrix, but can be converted into an oil-soluble form, i.e. a form which is soluble in the polymer matrix (=dye D) by derivatization in accordance with a known method. In the case of customary cationic dyes, it is possible, for example, to exchange the anions for those anions which have long-chain alkyl radicals. Anions having long-chain alkyl radicals include, for example, the anions of long-chain carboxylic acids having 8 to 22 carbon atoms, mono- and dialkylphosphates having 4 to 22 carbon atoms per alkyl radical, alkylsulfonates having 8 to 22 carbon atoms, e.g. dodecylsulfonate. Accordingly, dyes with basic groups, which are usually present in protonated form in the aqueous phase, can be reacted with the acids of the abovementioned anions giving oil-soluble salts of the dyes. Analogously, dyes with acidic functional groups or with anionic groups, e.g. sulfate or carboxylate groups, can be converted into a monomer-soluble form using long-chain amines or ammonium salts which have at least one long-chain organic radical. Suitable long-chain carboxylic acids, or salts thereof are derived from fatty acids, such as capric acid, palmitic acid, stearic acid, oleic acid, linoleic acid and linolenic acid. Suitable amines are, for example, primary, linear or branched alkylamines having 8 to 22 carbon atoms in the alkyl radical.

To convert the water-soluble, ionic dyes into a monomer-soluble form, it is generally sufficient to mix the dye with the long-chain acid, or the long-chain amine or the respective salt of the acid or of the amine. Optionally, the components are suspended in a solvent or the monomers, and the mixture is heated until the dyes dissolve, usually with stirring and/or under an inert gas atmosphere. Suitable water-soluble anionic dyes are known and commercially available. These dyes are usually dyes of the abovementioned classes of dye, for example mono- or disazo dyes which in each case have at least one sulfonic acid group; triarylmethane dyes carrying sulfonic acid groups; copper phthalocyaninesulfonic acid; stilbene dyes or quinoline dyes containing sulfonic acid groups. The following Colour Index numbers may be mentioned by way of example:

Direct Yellow 4, 5, 11, 50, 127, 137, 147, 153;
Acid Orange 7, 8;
Direct Orange 15, 34, 102;
Direct Red 81, 239, 252–255;
Direct Violet 9, 51;
Acid Blue 9, 86;
Direct Blue 199, 218, 267, 273, 279, 281;
Acid Black 194, 208, 210, 221;
Direct Black 19, 161, 170 and 171.

Examples of cationic or basic dyes include, for example, azo- and disazo dyes having amino groups or ammonium groups, triarylmethane dyes, or amine dyes, methine and azamethine dyes, for example Basic Red 1, Basic Red 14, Basic Blue 7, Basic Blue 11, Basic Blue 26, Basic Violet 1, Basic Violet 4, Basic Violet etc.

Furthermore, the monomer-soluble dyes D also include complexes of basic and acidic dyes or complexes of anionic and cationic dyes, for example the complex of chrysoidine base and metanil yellow acid.

The type of polymer matrix which the dye-containing polymer forms is of secondary importance for the use according to the invention. The polymeric matrix can either be formed from polyesters or from polyamides, polyurethanes or polymers of ethylenically unsaturated monomers. It is essential that the dye can be homogeneously dispersed in the polymer matrix, and that the dye-containing polymer is suitable for the formation of a finely divided aqueous dispersion.

Aqueous dispersions of dye-containing polymers PD which are suitable according to the invention, and the polymer powders prepared therefrom are known from the prior art, for example from EP-A 691 390, DE-A 4 436 892, DE-A 19 521 500, EP-A 566 448, U.S. Pat. No. 4,680,332, EP-A 808 855, WO 99/40123, and the earlier application PCT/EP 99/07229. Express reference is hereby made to the entire contents of the disclosure of these specifications with regard to aqueous dispersions of dye-containing polymers and the polymer powders prepared therefrom.

The dye-containing polymer dispersions of EP-A 691 390 and of DE-A 4 436 892 are aqueous polymer dispersions whose polymer matrix is built up from ethylenically unsaturated monomers. They are usually prepared by firstly preparing a polymer in an organic solvent from the ethylenically unsaturated monomers, dissolving an organic dye in the solution of the polymer, and converting the resulting dye-containing solution into an aqueous dispersion (secondary dispersion). The dye-containing polymer dispersions of DE-A 19 521 500 are prepared in a comparable manner using a polyurethane instead of the polymer built up from ethylenically unsaturated monomers.

The dye-containing aqueous polymer dispersions of EP-A 566 448 and of U.S. Pat. No. 4,680,332 are emulsion polymers which have been impregnated with a solution of the organic dye in an organic solvent.

Of the aqueous dispersions of dye-containing polymers PD known from the prior art, preference is given to those whose polymeric matrix is built up from ethylenically unsaturated monomers. These polymers can generally be prepared without great expenditure and permit simple matching of the polymer to the requirements of the dye, in particular with regard to its solubility in the polymer matrix, and to the requirements of the cosmetic compositions. For the aqueous dispersions of the dye-containing polymer used according to the invention, it has proven favorable for the polymer particles of the dispersion to have a mean particle diameter $d_z$ in the range from 10 to 1000 nm, preferably in the range from 50 to 500 nm and in particular in the range from 50 to 400 nm. The mean particle diameter $d_z$ is the z-mean particle diameter determined by quasi-elastic dynamic light scattering (calculated by unimodal analysis of the autocorrelation function). To determine the z-mean particle diameter, use is usually made of a Coulter N4 Plus Particle Analyzer from Coulter Scientific Instruments. The measurements are usually made on dilute aqueous polymer dispersions (0.01% strength by weight) under normal conditions (1 bar, 25° C.). The particle diameter is very particularly preferably in the range from 100 to 300 nm. In addition, it has proven advantageous if the distribution of the particle sizes of the polymer particles is narrow, i.e. the ratio of the half-width of the distribution curve, determined by means of dynamic light scattering, of the polymer particle sizes to the mean particle size is small. The ratio of breadth of distribution to mean particle size $d_z$ preferably has values of $\leq 1$, in particular $\leq 0.75$ and particularly preferably $\leq 0.5$.

In addition, it has proven advantageous for the glass transition temperature of the polymeric matrix $T_g$ to be at least 40° C., preferably at least 50° C. and in particular at least 60° C. The glass transition temperature here and below is the "mid-point temperature" determined in accordance with ASTM D 3418-82 by means of differential thermoanalysis. An estimate of the glass transition temperature for polymers built up from monoethylenically unsaturated monomers is possible with reference to the respective monomer composition using the Fox equation (see e.g. Ullmann's Encyclopedia of Industrial Chemistry 5 ed, Vol. A21, S. 169). A high glass transition temperature is advantageous particularly for cosmetic compositions whose constituents are melted during preparation.

Of the dye-containing polymers PD whose polymeric matrix is built up from monoethylenically unsaturated monomers M, the aqueous dye-containing polymer dispersions known from WO 99/40123, in particular, and the polymer powders obtainable therefrom are particularly preferred.

Such polymers PD comprise, in the form of their aqueous dispersions, dye-containing polymer particles having an average particle size $d_{50}$ of $\leq 1000$ nm. The polymer particles are built up from ethylenically unsaturated monomers M and comprise, in their polymeric matrix, at least one oil-soluble dye, i.e. a dye of at least limited solubility in the monomers M, in homogeneous, i.e. molecularly disperse distribution. In addition, the polymer matrix of such polymers often comprises at least one crosslinking monomer in copolymerized from.

The aqueous dispersions of dye-containing polymers described in WO 99/40123 frequently also satisfy the above preferred requirements for the particle size and the requirements for the uniformity of the polymer particles. In addition, the organic dyes are distributed particularly uniformly within the polymer matrix of such polymer particles and are also bonded particularly well in the polymer matrix. For further details with regard to the dye-containing polymers PD, the polymer powders prepared therefrom, and the preparation of the dye-containing aqueous polymer dispersions of the polymers PD and the preparation of the polymer powders of the dye-containing polymers PD, reference is made to WO 99/40123, to the entire contents of the disclosure of which reference is hereby made.

The polymeric matrix of the dye-containing polymers known from WO 99/40123 is generally built up from ethylenically unsaturated monomers M which include at least one hydrophobic monomer A having a solubility in water in the range from 0.01 to 60 g/l, in particular 0.1 to 50 g/l (at 25° C. and 1 bar). The monomers A generally constitute at least 50% by weight, preferably at least 70% by weight and in particular at least 80% by weight, based on the total weight of the monomers M.

The monomers A are preferably chosen from i) esters of $\alpha,\beta$-ethylenically unsaturated $C_3$–$C_8$-monocarboxylic acids and $C_4$–$C_8$-dicarboxylic acids with $C_1$–$C_8$-alkanols or $C_5$–$C_8$-cycloalkanols. Examples of these mono- and dicarboxylic acids are acrylic acid, methacrylic acid, crotonic acid, maleic acid, fumaric acid, itaconic acid and citraconic acid, preference being given to acrylic acid and methacrylic acid. Examples of $C_1$–$C_8$-alkan ols are methanol, ethanol, n-propanol, i-propanol, n-butanol, isobutanol, sec-butanol, t-butanol, 2-ethylhexanol and n-octanol. Examples of $C_5$–$C_8$-cycloalkanols are cyclopentanol and cyclohexanol. Preferred esters are methyl methacrylate, n-butyl methacrylate, methyl acrylate, ethyl acrylate, n-buty l acrylate, cyclohexyl acrylate and 2-ethylhexyl acrylate;

ii) vinyl esters of $C_1$–$C_8$-monocarboxylic acids. Examples of vinyl esters are vinyl acetate, vinyl propionate, vinyl butyrate and vinyl hexanoate;

iii) vinylaromatic compounds, such as styrene and $\alpha$-methylstyrene;

iv) $C_2$–$C_6$-olefins, such as ethylene, propene, 1-butene, 2-butene and isobutene.

It has proven advantageous for the monomers M also to comprise, in addition to the monomers A, crosslinking monomers, or monomers having a crosslinking action, B. As a result of the monomers B, better binding of the dye into the dye-containing polymers PD is achieved. The monomers B generally constitute 0.1 to 30% by weight, preferably 0.5 to 20% by weight, in particular 1 to 10% by weight, of the monomers M.

The monomers B are in particular monomers B1 which have at least 2 nonconjugated double bonds. Such monomers B1 are, if desired, used in an am ount of from 0.1 to 30% by weight, based on the total amount of the monomers to be polymerized, in particular 0.5 to 20% by weight and very particularly preferably 1 to 10% by weight.

Suitable monomers B1 include, for example, the vinyl, allyl and methallyl esters of the abovementioned ethylenically unsaturated carboxylic acids, and also the esters of these acids with tricyclodecenyl alcohol, in particular the esters of methacrylic acid and of acrylic acid, the esters of the abovementioned ethylenically unsaturated carboxylic acids with polyhydric alcohols, such as ethylene glycol diacrylate, ethylene glycol dimethacrylate, butanediol diacrylate, butanediol dimethacrylate, hexanediol diacrylate, hexanediol dimethacrylate, triethylene glycol diacrylate, triethylene glycol trimethacrylate, tris(hydroxymethyl)ethane triacrylate and trimethacrylate, pentaerythritol triacrylate and trimethacrylate, and also the allyl and methallyl esters of polyfunctional carboxylic acids, such as diallyl maleate, diallyl fumarate, diallyl phthalate. Typical monomers B1 are also compounds such as divinylbenzene, divinylurea, diallylurea, triallyl cyanurate, N,N'-divinyl and N,N'-diallylimidazolidin-2-one, and methylenebisacrylamide and methylenebismethacrylamide.

The monomers B also include monoethylenically unsaturated compounds B2 which, instead of at least one further ethylenically unsaturated bond, have a functional group which is in a position to subsequently crosslink the polymer or to react with a functional group of the dye which did not belong to the chromophore of the dye. Such functional groups are usually chosen from epoxy, hydroxy, N-methylol or carbonyl groups. Examples of monomers B are N-alkylolamides of the abovementioned ethylenically unsaturated carboxylic acids, e.g. N-methylol(meth)acrylamide, the hydroxyalkyl esters of the abovementioned ethylenically unsaturated carboxylic acids, in particular hydroxyethyl (meth)acrylate, the bisacetonylamides of the abovementioned ethylenically unsaturated carboxylic acids, in particular N,N-bisacetonyl(meth)acrylamide, and also the vinyl, allyl and methallyl glycidyl ethers, glycidyl esters of the abovementioned ethylenically unsaturated carboxylic acids, such as glycidyl (meth)acrylate, and also the esters of acetylacetic acid with the hydroxyalkyl esters of the abovementioned ethylenically unsaturated carboxylic acids, e.g. acetylacetoxyethyl (meth)acrylate.

Said monomers B2 can, if desired, be copolymerized in amounts of from 0.1 to 30% by weight, preferably 0.5 to 20% by weight, in particular 1 to 10% by weight, based on the total amount of the monomers to be polymerized. The total amount of monomers B1 and B2 is usually 30% by weight, preferably 20% by weight and in particular 10% by weight, based on the total amount of the monomers M.

With regard to the ability of the novel dye-containing aqueous polymer dispersions of the polymer PD to be prepared, it has furthermore proven advantageous for particularly hydrophobic monomers having a solubility in water of <0.01 g/l (at 25° C. and 1 bar) (monomers C) to be present during the polymerization of the monomers M. Monomers C are, if desired, used in an amount of from 0.1 to 20% by weight, in particular in an amount of from 1 to 10% by weight, based on the monomers M.

Examples of monomers C which have a low solubility in water as required above are 2- and 4-n-butylstyrene, p-tert-butylstyrene, esters of $\alpha,\beta$-monoethylenically unsaturated carboxylic acids having 3 to 6 carbon atoms and alkanols having $\geq 12$ carbon atoms (usually up to 30 carbon atoms), such as, for example, lauryl acrylate and stearyl acrylate. However, esters of vinyl alcohol or allyl alcohol and alkanecarboxylic acids having $\geq 9$ carbon atoms (as a rule up to 30 carbon atoms), such as, for example, vinyl nonanoate, vinyl decanoate, vinyl laurate and vinyl stearate, and commercially available monomers VEOVA® 9–11 (VEOVA X is a tradename of Shell and stands for vinyl esters of carboxylic acids which are also referred to as Versatic® X acids) of such monomers C. However, macromonomers such as oligopropene acrylate are also such monomers C (in very general terms, macromonomers are polymeric or oligomeric compounds which have at least one, in most cases, terminal, ethylenically unsaturated double bond; their relative number-average molecular weight should preferably be no more than 100000 for applicability as monomer C having as low a solubility in water as possible; as a rule, this relative number-average molecular weight will be 1000 to 50000 or 2000 to 50000; macromonomers are known to the person skilled in the art; their preparation is described, for example, in Makromol. Chem. 223 (1994) p. 29 to 46). Very generally, suitable monomers C having as low a solubility in water as possible are all those whose molar solubility at 25° C. and 1 atm in water equals or is less than the corresponding solubility of lauryl acrylate. Such monomers C are, for example, also methacryloyl polybutyl acrylate AB-6 and methacryloyl polystyrene A5-6 from Toa Gosei Kagaku KK (JP), which both have a number-average relative molecular weight of 6000. However, Polyol 130 and Polyol 110 from Hüls AG (stereospecific low-viscosity polybutadiene (75% 1,4-cis, 24% 1,4-trans, 1% vinyl), whose dynamic viscosity at 20° C. is 3000 mpas) also form monomers C which can be used as macromonomers having low solubility in water. Instead of the polymers C, it is also possible to use nonpolymerizable compounds having a solubility in water of <0.01 g/l during the preparation of polymers PD.

The monomers M can furthermore also comprise those monomers D whose homopolymers have an increased solubility in water (i.e. >60 g/l at 25° C.). Such monomers D serve as modifying monomers and are—if required— usually used in amounts of v 30% by weight, based on the total amount of the monomers to be polymerized, preferably v 20 and in particular v 10% by weight, for example in amounts of from 0.1 to 20% by weight, especially 0.5 to 10% by weight, based on the monomers to be polymerized. The monomers D include both monoethylenically unsaturated monomers having at least one acid group, e.g. a COOH, $SO_3H$ or a $PO_3H_2$ group, which can also be present in salt form (referred to below as anionic monomers); monoethylenically unsaturated cationic monomers, in particular those having a quaternary ammonium group (i.e. a $R_3N^\oplus$ group in which R is hydrogen or alkyl, in particular methyl or ethyl) or an immonium group (i.e. a $=N^\oplus(R)$ group in which R is hydrogen or alkyl, in particular methyl or ethyl); and monoethylenically unsaturated neutral monomers.

Examples of monoethylenically unsaturated anionic monomers D (monomers DA) are monoethylenically unsaturated mono- and dicarboxylic acids having 3 to 6 carbon atoms, e.g. acrylic acid, methacrylic acid, maleic acid, itaconic acid, acrylamidoglycolic acid, methacrylamidoglycolic acid, acryloyloxyglycolic acid, methacryloyloxyglycolic acid, monoethylenically unsaturated sulfonic acids and phosphonic acids, e.g. vinylsulfonic acid, allylsulfonic acid, methallylsulfonic acid, styrenesulfonic acid, vinylnaphthalenesulfonic acid and (meth)acrylamido-2-methylpropanesulfonic acid, also vinylphosphonic acid, allylphosphonic acid, methallylphosphonic acid, styrenephosphonic acid, and (meth)acrylamido-2-methylpropanephosphonic acid, and water-soluble salts thereof, e.g. alkali metal salts thereof or ammonium salts thereof, in particular sodium salts thereof. Examples of neutral monomers D (monomers DN) are in particular the amides of monoethylenically unsaturated mono- and dicarboxylic acids, such as acrylamide, methacrylamide and maleimide, also N-vinyllactams having 3 to 8 carbon atoms, such as N-vinylpyrrolidone and N-vinylcaprolactam, and acrylonitrile. Suitable cationic monomers D (monomers DC) are in particular the quaternization products and protonation products of monoethylenically unsaturated amines, for example the quaternization products of dialkylaminoalkyl esters of monoethylenically unsaturated carboxylic acids, e.g. the quaternization products of dimethylaminoethyl acrylate or methacrylate, and of diethylaminoethyl acrylate or methacrylate, and the quaternization products of 1-vinylimidazoles, such as 1-vinylimidazole and 1-vinyl-2-methylimidazole with $C_2$–$C_{10}$-oxiranes, $C_1$–$C_{10}$-alkyl halides or $C_1$–$C_{10}$-dialkyl sulfates, for example with methyl halide, ethyl halide, methyl sulfate or ethyl sulfate. Such monomers are known, for example, from EP-A 246 580 and U.S. Pat. No. 4,859,756. The quaternization products of 1-vinylimidazoles are also referred to below as vinylimidazolium salts, and the quaternization products of aminoalkyl acrylates or methacrylates are referred to as (meth)acryloyloxyalkylammonium salts. The monomers DN also include acrylonitrile and methacrylonitrile, the use of which frequently leads to better solubility of the dye in the monomers M and thus to better distribution of the dye in the polymeric matrix. Acrylonitrile and methacrylonitrile are, if desired, frequently used in amounts up to 50% by weight, in particular in amounts of from 0.5 to 30% by weight, based on the total weight of the monomers M, in the preparation of the dye-containing polymers PD.

Of the abovementioned polymers, preference is given for the use according to the invention in particular to those dye-containing polymers PD in which 50% by weight of the monomers A are chosen from monomers whose homopolymers have a glass transition temperature of >40° C. (monomers A1) and less than 50% by weight, in particular less than 30% by weight and particularly preferably less than 10% by weight, of those monomers A whose homopolymers have a glass transition temperature of <40° C. Examples of particularly preferred monomers A1 are methyl acrylate, methyl methacrylate, ethyl methacrylate, tert-butyl acrylate, vinyl acetate, styrene, vinyltoluene and methacrylonitrile, where the abovementioned monomers A can be replaced up to an amount of 50% by weight, based on the total amount of monomers, by acrylonitrile.

In a very particularly preferred embodiment of the novel dye-containing polymers, the polymeric matrix is built up from:

80 to 99% by weight of monomers A, in particular monomers A1, particularly preferably from methyl acrylate, styrene, methyl methacrylate or mixtures thereof, where up to 50% by weight of the monomers A1 can be replaced by acrylonitrile, 1 to 20% by weight, in particular 2 to 10% by weight, of monomers B, e.g. divinylbenzene or 1,4-butanediol diacrylate, 0 to 20% by weight, e.g. 1 to 20% by weight, of monomers C, e.g. lauryl acrylate or stearyl acrylate, and 0 to 20% by weight, e.g. 1 to 20% by weight, of monomers D, e.g. acrylic acid, methacrylic acid, acrylamide, methacrylamide, acrylamido-2-methylpropanesulfonate sodium salt.

The aqueous dispersions of dye-containing polymers PD known from WO 99/40123 are generally prepared by free-radical aqueous emulsion polymerization of an oil-in-water emulsion of the monomers M, in which the monomer droplets (=emulsion droplets) comprise the dye in dissolved form. The droplets preferably have a mean particle diameter $d_z$ of $\leq 500$ nm and in particular $\leq 400$ nm. $d_z$ will usually be at least 40 nm and preferably at least 100 nm. The particle size of the oil-in-water emulsion of the monomers is determined in a similar way to the particle size of the polymer particles of the polymer PD by quasielastic dynamic light scattering. The droplets in the dye-containing monomer emulsion preferably have a largely uniform size, i.e. the quotient $(d_{90}-d_{10})/d_{50}$ has a value of v 1, preferably $\leq 0.5$, in particular v 0.25. Here, $d_n$ stands for the particle diameter below which n % by weight of the emulsion droplets fall.

To prepare the dye-containing monomer emulsions in which the emulsion droplets comprise the dye in dissolved form or in molecularly disperse distribution, the dye is firstly dissolved in the monomers M to be polymerized. The resulting dye solution is then converted into an oil-in-water emulsion by customary methods, for example by stirring or dispersing it into an aqueous solution of a surface-active substance. The resulting aqueous emulsions generally have mean particle sizes $d_z$ above 1000 nm. It has proven successful to convert these "macroemulsions" into monomer emulsions having droplet sizes of to $\leq 500$ nm. The polymerization of monomer emulsions having droplet sizes of $\leq 500$ nm leads to particularly high-value dye-containing polymers PD. Such monomer emulsions are also referred to as "mini-emulsions" (cf. P. L. Tang, E. D. Sudol, C. A. Silebi and M. S. El-Aasser in Journal of Applied Polymer Science, Vol. 43, p. 1059–1066 [1991]). For this purpose, the conventional monomer emulsions are preferably homogenized prior to the polymerization to give mini-emulsions.

The homogenization is preferably carried out using ultrasound (e.g. Branson Sonifier II 450). For the homogenization using ultrasound, the instruments described in GB 22 50 930 A and U.S. Pat. No. 5,108,654, for example, are suitable. The use of ultrasound has proven particularly successful for the preparation of the dye-containing mini-emulsions and generally leads to particularly high-value dye-containing polymers PD. Accordingly, preference is given according to the invention to those preparations in which the dye-containing polymer PD is obtainable by polymerization of a mini-emulsion, where the mini-emulsion is obtainable by:

i) dissolving the dye D in the monomers M1,
ii) producing a conventional, dye-containing emulsion by emulsifying the monomers in the presence of at least one surface-active compound, and
iii) homogenizing the conventional emulsion by means of ultrasound to give a dye-containing mini-emulsion.

For details regarding the preparation of the mini-emulsions, reference is made at this point to WO 99/40123, to the entire contents of the disclosure of which reference is made.

Suitable surface-active substances for the preparation of the emulsions are, in principle, all surface-active substances for emulsion polymerization, preference being given to neutral, anionic and cationic emulsifiers, and neutral, anionic or cationic protective colloids.

The nature of the surface-active substance is given essentially by the requirements of the cosmetic application and, with regard to the preparation of the dye-containing polymers, is rather insignificant.

Examples of emulsifiers and protective colloids which are suitable both for cosmetic applications and for the preparation of the polymers PD are given below:

Anionic emulsifiers are, for example, alkali metal and ammonium salts of alkyl sulfates (alkyl radical: $C_8$ to $C_{20}$), of sulfuric half-esters of ethoxylated alkanols (degree of EO: 4 to 30, alkyl radical: $C_{10}$ to $C_{20}$), of sulfuric half-esters of ethoxylated alkylphenols (alkyl radical: $C_4$ to $C_9$; degree of EO: 3 to 50), of sulfonated fatty acids, of di-$C_4$–$C_{20}$-alkyl esters of sulfosuccinic acid and similar compounds.

Examples of suitable neutral emulsifiers are ethoxylated mono-, di- and trialkylphenols (degree of EO: 3 to 50, alkyl radical: $C_4$ to $C_9$), ethoxylated fatty alcohols (degree of EO: 3 to 50, alkyl radical: $C_8$ to $C_{36}$), ethoxylated oxo alcohols (degree of EO: 3 to 50, alkyl radical: $C_8$ to $C_{36}$), ethoxylated glycerides of fatty acids (degree of EO: 3 to 50, fatty acid radical).

Examplels of cationic emulsifiers are alkylammonium halides having at least one long-chain alkyl group, e.g. dodecyltrimethylammonium chloride, bromide, cetyltrimethylammonium chloride or bromide, dimethyl-$C_{12}/C_{14}$-alkylbenzylammonium chloride or bromide.

Further suitable emulsifiers are given in Houben-Weyl, Methoden der organischen Chemie [Methods of Organic Chemistry], Volume XIV/1, Makromolekulare Stoffe [Macromolecular Substances], Georg-Thieme verlag, Stuttgart, 1961, pp. 192–208, and in Ullmann's Encyclopedia of Industrial Chemistry, 5th ed., VCH Weinheim 1987, Vol. 9a, pp. 313–318.

Protective colloids are water-soluble organic polymers. These are barely able to reduce the surface tension of water and, in contrast to emulsifiers, generally have relative molecular weights above 1000, preferably above 2000.

Examples of cationic protective colloids are the homo- and copolymers of monoethylenically unsaturated cationic monomers, for example homo- and copolymers of quaternized N-vinylimidazoles or of quaternized dialkylaminoalkyl acrylates or methacrylates with, for example, N-vinylpyrrolidone and/or N-vinylcaprolactam. Further examples include cationically modified starches.

Neutral protective colloids are, for example, polyvinyl alcohols, partially hydrolyzed homo- and copolymers of vinyl acetate, ehylene oxide/propylene oxide block copolymers, modified starches, cellulose derivatives, polyvinylpyrrolidone, and copolymers of vinylpyrrolidone with neutral monomers, e.g. with vinylcaprolactam, vinyl acetate, acrylamide, methacrylamide, methyl acrylate, ethyl acrylate, n-butyl acrylate or with methyl methacrylate.

Examples of anionic protective colloids are homo- and copolymers of monoethylenically unsaturated carboxylic acids and salts thereof, in particular sodium and ammonium salts thereof, e.g. homo- and copolymers of acrylic acid, of methacrylic acid or of maleic acid, optionally with neutral comonomers chosen from the abovementioned monomers A and the monomers D2, e.g. from styrene, esters of (meth) acrylic acid, vinyl acetate, acrylamide, methacrylamide, acrylonitrile and hydroxyalkyl (meth)acrylates. Anionically protective colloids are also anionically modified starches and starch degradation products.

The abovementioned surface-active substances naturally remain in the aqueous dispersions of the dye-containing polymer PD following preparation and determine its application properties.

These particularly preferred aqueous polymer dispersions of the dye-containing polymers PD are prepared then by reacting the dye-containing emulsions, preferably the above-described mini-emulsions, with a free-radical polymerization initiator. One possible procedure is to initially introduce the dye-containing emulsion, preferably in the form of a mini-emulsion, into the reactor and to add thereto the polymerization initiator under polymerization conditions in one portion or in two or more portions or continuously at the rate of its consumption. It is also possible to firstly add some or all of the polymerization initiator to the amount of emulsion, and then to heat the mixture to the polymerization temperature.

It is also possible to add some or all of the aqueous dye-containing monomer emulsion, preferably in the form of a mini-emulsion, to the polymerization vessel under polymerization conditions according to the progress of the reaction. Preferably, the polymerization initiator is introduced into the polymerization vessel at least partially in parallel to the addition of the monomer emulsion.

Suitable free-radical polymerization initiators are, in principle, all those which are able to trigger a free-radical polymerization. These are peroxides, hydroperoxides and also azo compounds. The free-radical polymerization initiators can either be water-soluble or oil-soluble, i.e. soluble in the monomers. Examples of water-soluble initiators are peroxodisulfuric acid and its ammonium and alkali metal salts, hydrogen peroxide or low molecular weight hydroperoxides, such as tert-butyl hydroperoxide, or salt-like azo compounds, e.g. 2,2'-azobis-2-amidinopropane dihydrohalide.

Examples of oil-soluble polymerization initiators are $C_4$–$C_{12}$-peroxocarboxylic acids and their esters, e.g. peroctoates and perbenzoates, such as tert-butyl peroctoate and tert-butyl perbenzoate, and diacyl peroxides, such as dibenzoyl peroxide.

The abovementioned water-soluble peroxidic polymerization initiators can also be combined with a reducing agent and optionally with a metal compound soluble in the aqueous medium (redox initiator systems). These are well known to the person skilled in the art. With regard to further details, reference is made to WO 99/40123.

The amount of initiator used is generally in the range from 0.1 to 10% by weight, preferably 0.2 to 8% by weight and frequently in the range from 0.3 to 5% by weight.

In the preparation of the particularly preferred aqueous dispersions of the dye-containing polymers PD, the polymerization temperatures are primarily governed in a known manner by the redox initiator system used in each case. The polymerization temperatures usually lie in the range from 0 to 95° C., preferably in the range from 30 to 90° C. If an increased pressure is used, the polymerization temperature can also be up to 120° C. Polymerization is usually carried out at atmospheric pressure (1 atmosphere).

According to the invention, the finely disperse dye-containing polymer, instead of being used in the form of an aqueous polymer dispersion, can also be used in the form of a polymer powder obtainable from this aqueous polymer dispersion. Methods for the preparation of polymer powders from aqueous polymer dispersions are already known to the person skilled in the art. The preparation usually takes place by spray-drying, optionally in the presence of spray auxiliaries, in a warm stream of air, or by freeze-drying. Methods of spray-drying and freeze-drying are known in principle to the person skilled in the art and can be applied to the drying of the above-described polymer dispersions.

Spray-drying involves, for example, spraying the polymer dispersions to be dried in a customary drying tower in a stream of warm air. In this connection, the inlet temperature of the stream of warm air is in the range from 100 to 200° C., preferably 120 to 160° C., and the outlet temperature of the stream of warm air is in the range from 30 to 90° C. and preferably 60 to 80° C. The spraying of the aqueous polymer dispersion in the stream of warm air can, for example, be carried out using single-component or multi-component nozzles or via a rotating disk. The polymer powders are usually separated off using cyclones or filter separators. The sprayed aqueous polymer dispersion and the stream of warm air are preferably introduced in parallel.

Suitable spray auxiliaries, which are also referred to as drying auxiliaries, are either neutral, cationic, anionic or amphoteric water-soluble polymers. These usually have a molecular weight $M_N$ in the range from 1000 to 1000000, preferably 2000 to 100000. Examples of such polymers are the polymers given above as protective colloids.

Specific examples of neutral polymers are: polyvinyl alcohols (see e.g. EP-A-56 622, EP-A-680 993, DE-A-22 14 410 and DE-A-26 14 261), polyvinylpyrrolidones (see e.g. DE 22 38 903 and EP 576 844). Examples of anionic polymers are phenolsulfonic acid/formaldehyde condensates (see e.g. EP-A 407 889, WO 98/03576), naphthalenesulfonic acid/formaldehyde condensates (see e.g. WO 98/03577), homo- and copolymers of 2-acrylamido-2-methylpropanesulfonic acid (see e.g. EP-A 629 650, EP-A 671 435 and DE-A 195 39 460), copolymers of ethylenically unsaturated carboxylic acids, such as, in particular, acrylic acid, methacrylic acid and maleic acid, with hydrophobic comonomers, such as styrene (see e.g. EP 467 103) or olefins (see e.g. EP 9 169) or with hydroxyalkyl esters (see e.g. JP 59 162 161). Examples of cationic polymers are copolymers and terpolymers of vinylpyrrolidone and/or of vinylcaprolactam with 1-vinyl-3-alkylimidazolinium salts, e.g. with 1-vinyl-3-methylimidazolinium chloride or methosulfate; copolymers and terpolymers of vinylpyrrolidone and/or of vinylcaprolactam with (meth)acryloyloxyethyltrialkylammonium salts or with (meth) acryloyloxyethylammonium salts. Such cationic polymers are known to the person skilled in the art and are available commercially.

Suitable amphoteric polymers are copolymers of acrylic acid and optionally hydrophobic monomers such as styrene and optionally water-soluble, neutral monomers with the cationic monomers DC given under D, e.g. copolymers of acrylic acid with styrene and with (meth) acryloxyethyltrialkylammonium salts, and optionally with further comonomers such as (meth)acrylamide and acetonitrile. Such copolymers are known, for example, from EP-A 51 144.

The aqueous dispersions or powders of the dye-containing polymers PD used according to the invention can be incorporated into cosmetic compositions in a known manner. The nature of the cosmetic composition determines whether aqueous dispersions or powders are preferred. Incorporation into the cosmetic composition takes place by the procedures customary for this purpose, usually by stirring or homogenizing into the other constituents of the cosmetic composition. In contrast to the commercially available pigments, digestion of the powder is not necessary.

Examples of cosmetic compositions which are formulated as decorative cosmetic compositions are compositions for the treatment of facial skin, in particular in the eye area, such as kohl pencils, eyeliner pencils, eyebrow pencils, eye shadows, cream blusher, powder blusher, foundation, make-up, e.g. stage make-up, lipsticks, compositions for treating eyebrows and eyelashes, such as mascara and eyelash make-up; nail varnishes, both solvent-based and water-based; hair treatment compositions, such as hair gels, e.g. wet gel, styling gel, hair sprays, hair mascara, styling mousse, hair foam, hair shampoo; and also colored soaps; sunscreens, e.g. sunblock creams and sunblock sticks. The latter contain at least on polymer PF, which comprises one of the above mentioned UV absorbers as a dye F. Preferably, the amount of UV absorbers in such polymers PF is in the range of from 5 to 30% by weight, based on the weight of the polymer matrix. The amount of polymer PF naturally depends on the desired sun protection factor (SPF) and on the amount of UV absorber in the polymer PF.

For water-based cosmetic compositions, for example aqueous nail varnishes, mascara, foundations of the O/W type or foundations of the W/O type, for decorative hair care compositions, such as wet gel, styling gel, hair spray, hair mascara, or styling mousse, preference is given, for the sake of simplicity, to using aqueous dispersions of the dye-containing polymers PD. In contrast, for cosmetic compositions which consist exclusively of oils or fats, in particular those which have a solid form, e.g. pencils, such as kohl pencils, eyeliner pencils, eyebrow pencils, stick stage make-up, lipsticks and the like, and for powder or fine powder cosmetic compositions such as eye shadows and cream blusher or loose powder blusher, use is made of a pulverulent dye-containing polymer PD.

The amount of dye-containing polymer PD in the cosmetic compositions is primarily governed by the desired color impression which the decorative cosmetic composition is to have. Depending on the nature of the cosmetic composition and of the desired color impression, the content of dye-containing polymer in the cosmetic composition is in the range from 0.1 to 50% by weight, based on the total weight of the cosmetic composition.

In the case of nail varnishes, 1 to 10% by weight, for example, based on the nail varnish, of dye-containing polymer PD is used. In the case of mascara and eyelash make-up, 2 to 20% by weight, based on the cosmetic composition, of at least one dye-containing polymer PD is generally used as color-imparting constituent. In cosmetic pencils, such as kohn pencils, eyeliner pencils, eyebrow pencils, eye shadow pencils, 10 to 40% by weight of dye-containing polymer is generally used. In the case of eye shadows, the content of polymer PD is usually higher still and can be as much as 50% by weight. In the case of cream blusher and loose powder blusher, the content of dye-containing polymer PD is frequently in the range from 1 to 20% by weight, in particular in the range from 2 to 15% by weight. In the case of lipsticks, use is frequently made, depending on the desired color impression, of 2 to 40% by weight, in particular 5 to 30% by weight, of dye-containing polymer, based on the total weight of the lipstick. In the case of hair gel and styling gel and in the case of hair spray, use is generally made of lower contents of dye-containing polymer PD, e.g. 0.1 to 10% by weight, in particular 0.5 to 5% by weight.

It is of course also possible to additionally use other pigments of the prior art, in which case these can partially replace the dye-containing polymers PD, or can supplement them to change the color impression. In the cosmetic compositions according to the invention, the amount of additional prior art pigments is generally in the range from 0.1 to 30% by weight, based on the total weight of the cosmetic composition, and is naturally governed by the nature of the cosmetic composition and by the desired color impression.

The finely disperse dye-containing polymers PD used in accordance with the invention have, compared with the prior art pigments, firstly the advantage that they can be incorporated into the cosmetic compositions more readily since grinding and digestion of the pigment is not required. It is true both for the aqueous polymer dispersions and also for the powders of the polymer PD. The possible use of aqueous polymer dispersions facilitates in particular also the preparation of formulations which have a high water content and a low or no fat content. In addition, the dye-containing polymers PD have a higher color depth than comparable pigments of the prior art. In contrast to pigments of the prior art, if the shade of the cosmetic composition is changed, it is not necessary to specifically adapt the other constituents to the new color-imparting constituent. Since it is possible to incorporate the most varied dyes into one type of polymer matrix, by matching the polymer matrix to the respective cosmetic composition once, it is possible to provide a broad palette of colorants.

The cosmetic composition according to the invention can be in the form of a suspension or dispersion in solvent or fatty substances, in the form of an emulsion, such as, for example, in the of a cream or in the form of a milk, in the form of a pomade, gel or in the form of a solid stick; it can be formulated as an aerosol or be in the form of a foam.

The cosmetic composition comprises the cosmetic adjuvants customary for the respective type of composition. Examples of customary cosmetic ingredients, and numerous formulation examples of cosmetic compositions are given in K. Schrader, Grundlagen und Rezepturen der Kosmetika [Cosmetics Principles and Formulations], $2^{nd}$ edition, H üthig-Buchverlag, Heidelberg, 1989.

Ingredients which are in principle present in the cosmetic compositions of the invention include solvents, such as water, lower monoalcohols or polyols having 1 to 6 carbon atoms or mixtures thereof; the particularly preferred monoalcohols or polyols are ethanol, isopropanol, propylene glycol, glycerol and sorbitol; also present are fatty substances, such as mineral, animal, vegetable or synthetic oils or waxes, fatty acids, fatty acid esters, such as triglycerides of $C_6$–$C_{12}$-fatty acids, fatty alcohols, vaseline, paraffin, lanolin, hydrogenated lanolin, acetylated lanolin and silicone oil.

The cosmetic composition usually comprises the cosmetic adjuvants customary for the respective type of composition, such as thickeners, emollients, hydrating products, interface-active agents, preservatives, sequestering agents, antioxidants, antifoams, oils, waxes, lanolin, perfumes, propellants, dyes, vitamins or other ingredients customarily used in cosmetics.

If the composition is formulated as an aerosol, use is made of classical propellants, such as alkanes, dinitrogen oxide and dimethyl ether.

Emulsions in the form of a cream or a make-up comprise, apart from the polymers PD, fatty alcohols, fatty acid esters and, in particular, fatty acid triglycerides, fatty acids, lanolin and derivatives, natural or synthetic oils or waxes and emulsifiers in the presence of water.

The concentration of the emulsifier system is usually 4 to 35%, based on the total weight of the emulsion; the fatty phase frequently constitutes between 10 and 90%, and the aqueous phase between 10 and 90%, based on the total weight of the emulsion. The emulsifiers are those customarily used in this type of emulsion. In particular, they are chosen from:

$C_{12}$–$C_{18}$ sorbitan fatty acid esters, esters of hydroxystearic acid and $C_{12}$–$C_{30}$-fatty alcohols, mono- and diesters of $C_{12}$–$C_{18}$-fatty acids and glycerol or polyglycerol, condensates of ethylene oxide and propylene glycols, oxypropylenated/oxyethylenated $C_{12}$–$C_{20}$-fatty alcohols, polycyclic alcohols, such as sterols, aliphatic alcohols with a high molecular weight, such as lanolin, mixtures of oxypropylenated/polyglycerolated alcohols and magnesium isostearate, succinic esters of polyoxyethylated or polyoxypropylenated fatty alcohols, the lanolates and stearates of magnesium, calcium, lithium, zinc or aluminum, optionally as a mixture with hydrogenated lanolin, lanolin alcohol, or stearic acid or stearyl alcohol.

The fatty products of which the fatty phase of the emulsions consist, include:

hydrocarbon oils, such as paraffin oil, purcellin oil, perhydrosqualene and solutions of microcrystalline waxes in these oils, animal or plant oils, such as sweet almond oil, avocado oil, calophylum oil, lanolin and derivatives thereof, castor oil, horse oil, pig oil, sesame oil, olive oil, jojoba oil, karite oil, Hoplostethus oil, mineral oils whose distillation start-point under atmospheric pressure is about 250° C. and whose distillation end-point is at 410° C., such as, for example vaseline oil, esters of saturated or unsaturated fatty acids, such as alkyl myristates, e.g. isopropyl, butyl or cetyl myristate, hexadecyl stearate, ethyl or isopropyl palmitate, octanoic or decanoic triglycerides and cetyl ricinoleate.

The fatty phase can also comprise silicone oils which are soluble in other oils, such as dimethylpolysiloxane, ethylphenylpolysiloxane and the silicone glycol copolymer, fatty acids and fatty alcohols.

In order to favor the retention of oils, it is also possible to use waxes, such as, for example, carnauba wax, candellila wax, beeswax, microcrystalline wax, ozokerite wax and Ca, Mg and Al oleates, myristates, linoleates and stearates.

The emulsions can also be in the form of a stick. In this case, the concentration of the water phase in the emulsion is generally to 70% by weight, based on the total weight of the emulsion.

Fatty gels generally comprise an oil or a wax and a thickener, such as silica. The oily-alcoholic or aqueous-alcoholic gel comprise one or more lower alcohols and polyols, such as ethanol, propylene glycol or glycerol, a thickener, such as silica, cellulose derivatives, polyacrylic acid derivatives and guar, carob and xanthan gum in the presence of oils or of water.

Solid sticks generally consist of fatty substances, such as natural or synthetic waxes and oils, fatty alcohols, fatty acid esters and lanolin.

Cosmetic compositions based on water frequently comprise gel formers, such as hydrocolloids and semisolid fats and waxes, e.g. guar gum, xanthan gum, tragacanth, alginates, starch, starch derivatives, gelatin, cellulose and cellulose derivatives, such as methylcellulose, sodium carboxymethylcellulose, hydroxypropylcellulose, hydroxyethylcellulose and polyacrylate.

Hair-treatment compositions, in particular those based on alcohol or water, e.g. hair sprays, hair gels, such as wet gel or styling gel, frequently also comprise hair polymers for setting, improving structure or shaping.

Examples of hair polymers are, in particular:

nonionic, water-soluble or water-dispersible polymers or oligomers, such as polyvinylcaprolactam, e.g. Luviskol Plus (BASF), or polyvinylpyrrolidone and copolymers thereof, in particular with vinyl esters, such as vinyl acetate, e.g. Luviskol VA 37 (BASF); polyamides, e.g. based on itaconic acid and aliphatic diamines, as are described, for example, in DE-A-43 33 238;

amphoteric or zwitterionic polymers, such as the octylacrylamide/methyl methacrylate/tert-butylaminoethyl methacrylate/2-hydroxypropyl methacrylate copolymers obtainable under the name Amphomer® (National Starch), and zwitterionic polymers, as disclosed, for example, in German Patent Applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacroylethylbetaine/methacrylate copolymers, which are commercially available under the name Amersette® (AMERCHOL), and copolymers of hydroxyethyl methacrylate, methyl methacrylate, N,N-dimethylaminoethyl methacrylate and acrylic acid (Jordapon®);

anionic polymers, such as vinyl acetate/crotonic acid copolymers, as are commercially available under the names Resyn® (NATIONAL STARCH), Luviset® (BASF) and Gafset® (GAF), vinylpyrrolidone/vinyl acrylate copolymers, obtainable for example under the tradename Luviflex® (BASF). A preferred polymer is the vinylpyrrolidone/acrylate terpolymer obtainable under the name Luviflex® VBM-35 (BASF). Acrylic acid/ethyl acrylate/N-tert-butylacrylamide terpolymers sold, for example, under the name Ultrahold® strong (BASF), and Luvimer® (BASF, terpolymer of t-butyl acrylate, ethyl acrylate and methacrylic acid), sodium sulfonate-containing polyamides or sodium sulfonate-containing polyesters, or cationic (quaternized) polymers, e.g. cationic polyacrylate copolymers based on N-vinyllactams and derivatives thereof (N-vinylpyrrolidone, N-vinylcaprolactam etc.), and customary cationic hair conditioning polymers, e.g. Luviquat® (copolymer of vinylpyrrolidone and vinylimidazolium methochloride), Luviquat® Hold (copolymer of quaternized N-vinylimidazole, N-vinylpyrrolidone and N-vinylcaprolactam), Merquat® (polymer based on dimethyldiallylammonium chloride), Gafquat® (quaternary polymers formed by reacting polyvinylpyrrolidone with quaternary ammonium compounds), Polymer JR (hydroxyethylcellulose having cationic groups), polyquaternium grades (CTFA names) etc.;

nonionic, siloxane-containing water-soluble or -dispersible polymers, e.g. polyether siloxanes, such as Tegopren® (Goldschmidt) or Belsil® (Wacker).

The cosmetic compositions of the invention are prepared by incorporating the finely divided, dye-containing polymer PD, either as a powder or as an aqueous dispersion, into a base mixture of constituents customary for the respective type of composition. Incorporation is usually achieved by simply mixing the polymer PD with at least one constituent of the cosmetic composition or with a mixture of constituents of the cosmetic composition such as an O/W- or W/O-Emulsion, a melt, a powder, a gel, a solution or a fatty phase. Usually the obtained mixture is then homogenized. The finely divided, dye-containing polymer PD can either be incorporated as a powder or as an aqueous dispersion, depending on wether the constituent is a hydrophobic or hydrophilic liquid or a solid. The mixture is usually then further processed to obtain the cosmetic in a ready-to-use form according to known procedures. Methods of making cosmetic compositions are known from the art, e.g. from K.Schrader, Grundlagen und Rezepturen der Kosmetika [Cosmetics Principles and Formulations], $2^{nd}$ edition, H üthig-Buchverlag, Heidelberg, 1989 p. 905 to 935.

The examples given below of dye-containing polymers PD in the form of aqueous dispersions or powders, and the cosmetic formulation examples serve to illustrate the present invention in more detail.

Examples of polymers PD suitable according to the invention

I. General

The polymer particle size ($d_z$ value) was determined in the manner described above using a Coulter N4 Plus Particle Analyzer on 0.01% strength by weight sample of the dispersion.

Relative Light transmittance for white light (LD value) was determined on 0.01% strength by weight sample of the dispersion (path length of 2,5 cm relative to the light transmittance of pure water).

Viscosity was determined by using an Eprecht-type viscosimeter A-III at 23° C. for 20 min.

Dyes Used

Dye 1: Lumogenr F Yellow

083: 1,7-bis(isobutyloxycarbonyl)-6,12-dicyanoperylene

Dye 2: Lumogenr F Rot 300 (BASF; perylenetetracarboxylic diimide fluorescent dye);

Dye 3: C.I. Solvent Yellow 162;

Dye 4: Neopenr Cyan 742 (BASF; azamethine dye)

Dye 5: Neopenr Magenta 525 (BASF; azamethine dye)

Dye 6: Neopenr Blue FF 4012 (BASF; Cu phthalocyanine dye);

Dye 7: C.I. Solvent Red 119

Dye 8: C.I. Basic Red 14+dodecylsulfonate (1:1)*

Dye 9: Rhodamine 2C Base+oleic acid (1:1)*

* Components were used in the molar ratio 1:1

UV-Absorber 1: n-octyl 4-methoxycinnamate,

UV-Absorber 2: bis(2-ethylhexyl) 4,4-diphenylbutadiene-1,1-dicarboxylate,

UV-Absorber 3: 4-tert.-Butyl-4'-methoxydibenzoylmethan,

UV-Absorber 4: 2,4,6-Tris-{N-[4-(2-ethylhex-1-yl) oxycarbonylphenyl]amino}-1,3,5-triazin, UV-Absorber 5: 2'-ethylhexyl 2-cyano-3,3-diphenylacrylate (Octocrylen)

The following abbreviations are used:

AS: acrylic acid

BDDA: butanediol diacrylate

DVB: divinylbenzene

HD: hexadecane

L370: Luviquat® FC 370

MAA: methacrylic acid

MMA: methyl methacrylate

NaPS: sodium peroxodisulfate

NLS sodium lauryl sulfate (15% strength by weight)

CP: copolymer of 68% by weight of styrene, 10% by weight of acrylic acid and 22% by weight of N-(3-dimethylaminopropyl)methacrylamide (20% strength by weight in glacial acetic acid/water 1:6)

S: styrene

SA: stearyl acrylate

T: Tamol® NN4501

Luviquat® FC 370 is an approximately 40% strength by weight aqueous solution of a copolymer of vinylpyrrolidone and 1-vinyl-3-methylimidzolium chloride in the weight ratio 7:3 having a K value (in accordance with Fikentscher; determined in accordance with DIN 53726 as a 1% strength by weight solution in 3% strength by weight aqueous NaCl solution) in the range from 41 to 49 (manufacturer: BASF AG, Ludwigshafen).

Tamol® NN 4501 is the pulverulent sodium salt of a low molelcular weight formaldehyde condensation product of an isomeric mixture of α- and β-naphthalenesulfonic acid, this 45% strength by weight aqueous solution has a mean viscosity (in accordance with Brookfield) of about 70 mpa·s (determined at 23° C.) (manufacturer: BASF AG, Ludwigshafen).

II. Preparation of Aqueous Dispersions of Dye-containing Polymers (PD No. 1 to 10)

1. Preparation by Batch Process (General Procedure in Accordance with WO 99/40123 V 1., Polymers PD No. 6 to 10)

1.1 Preparation of the Dye-containing Miniemulsion

A reaction vessel fitted with stirrer was charged with 250 g of deionized water and 25 g of a 5% strength by weight solution of a copolymer CP as protective colloid. If $H_2O_2$ was used as initiator, 0.5 g of ascorbic acid and 0.5 g of a 1% strength by weight aqueous Fe EDTA solution were additionally added. (initial charge). A solution of the respective dye in the monomers to be polymerized (monomer/dye solution) was added thereto over the course of 2 minutes. The constituents of this solution are given in Table 1. If tert-butyl hydroperoxide was used as initiator, this was dissolved following dissolution of the dye in the monomers The mixture was then stirred for a further 10 minutes. The resulting conventional dye-containing monomer emulsions were then homogenized using ultrasound as follows to give an aqueous monomer micro emulsion:

The ultrasound source used was the instrument described in FIG. 4 of DE 197 56 874, fitted with a flow cell having a vessel diameter of 42 mm and a height of 25 mm. The sonotrode had a diameter of 40 mm and a power of 1000 W. In each case about 0.5 liter of the aqueous macroemulsion was sonicated with stirring at a throughput rate of 30 l/h at a power of 1000 W. This gave aqueous dye-containing micro emulsions.

1.2 Polymerization of the Dye-containing Miniemulsion

The resulting miniemulsion was introduced into a polymerization v essel and heated to 80° C. The initiator solution was then added in one portion with stirring, the mixture was left to postreact for 2.5 h at 80 to 85° C. and then cooled to 25° C. This gave an approximately 30 to 35% strength by weight aqueous dispersion of the polymer PD. The me an particle sizes of the resulting polymer dispersions are given in Table 1.

Initiator solution: 0.7 g of $H_2O_2$ in 28 g of water

2. Preparation by Feed Method (Polymer PD No. 1 to 5)

Firstly, in the manner described under II 1.1, 170 g of water, 2 g of a 15% strength by weight sodium lauryl sulfate solution and a solution of 10 g of Dye 2 and 1 g of t-BPO in 100 g of MMA and 5 g of BDDA were used to prepare a miniemulsion (Feed 1).

29 g of the resulting miniemulsion were mixed with 0.3 g of a 6% strength by weight aqueous ascorbic acid solution (Feed 2) and 0.3 g of a 1% strength by weight Fe EDTA solution. The mixture was heated to 80° C. and then, connecting simultaneously, the dye-containing miniemulsion and 5.3 g of Feed 2 were added to the polymerization vessel over the course of 1 h with retention of a temperature of 80° C., and then the mixture was left to afterpolymerize for 1 h after the addition was complete. The solids content of the dispersion was 39% by weight. The mean particle size was 200 nm.

The dye-containing polymers PD No. 2 to No. 5 were prepared in a similar manner.

The initiator used was a solution of 1 g of sodium peroxodisulfate in 39 g of water. The initial charge comprised 4 g of the initiator solution and 100 g of water.

Unless stated otherwise, the emulsifier used was the bis-2-ethylhexyl ester of sulfosuccinic acid (as sodium salt in the form of a 60% strength by weight aqueous solution) (LUMITEN® IRA from BASF AG), 0.6 g in the case of the preparation of polymer PD No.2 and 1.2 g in the case of polymer PD No. 3, 4 and 5. In the case of the preparation of polymer PD No. 3, 4.8 g of Tamol NN4501 was additionally used, and in the case of the preparation of PD No. 5, 4.8 g of Luviquat FC 370 were additionally used.

The particle sizes of the polymers PD are given in Table 1.

All of the polymers PD can be freeze-dried with cooling in a dry ice/acetone bath by applying a vacuum to give redispersible powders.

mately 20% strength by weight aqueous solution of the polymer PD. The formation of coagulum was low for every example (<5%, based on the reactants).

Light transmittance (LD value), pH value and viscosity of the thus obtained polymer dispersions are given in table 2. As a consequence of the preparation method the average particle diameter of the polymer particles were below 400 nm. The obtained dispersions showed a good storage stability and could be freeze-dried to polymer powders.

TABLE 1

| Polymer | Monomer A | | Monomer B | | Monomer C | | Monomer D | | Dye | Emulsifier | | $d_z$ | |
|---|---|---|---|---|---|---|---|---|---|---|---|---|---|
| PD No. | Type | [g] | Type | [g] | Type | [g] | Type | [g] | No. | [g] | Type | [nm] | Initiator/method |
| 1 | MMA | 95 | BDDA | 10 | — | — | — | — | 2 | 10 | NLS | 200 | t-BPO; feed |
| 2 | MMA | 95 | DVB | 5 | — | — | MAA | 10 | 3 | 5 | Lumiten | n.d. | NaPS; feed |
| 3 | MMA | 95 | DVB | 5 | AA | 5 | — | — | 4 | 10 | Lumiten + Tamol | 205 | NaPS; feed |
| 4 | MMA S | 60 35 | DVB | 5 | HD | 5 | AA | 5 | 5 | 10 | Lumiten | 182 | NaPS; feed |
| 5 | MMA | 90 | DVB | 5 | — | — | AA | 10 | 4 | 10 | Lumiten + L 370 | n.d. | NaPS; feed |
| 6 | S MMA | 60 35 | BDDA | 5 | AA | 5 | — | — | 6 | 5 | CP | 209 | $H_2O_2$; batch |
| 7 | MMA | 95 | BDDA | 5 | AA | 5 | — | — | 1 | 10 | CP | 188 | $H_2O_2$; batch |
| 8 | MA | 95 | BDDA | 5 | AA | 5 | — | — | 7 | 10 | CP | 179 | $H_2O_2$; batch |
| 9 | MMA | 100 | BDDA | 5 | — | — | — | — | 8 | 10 | CP | 211 | t-BPO; batch |
| 10 | MA | 100 | BDDA | 5 | SA | 5 | — | — | 9 | 10 | CP | 220 | $H_2O_2$; batch |

1) $d_z$ = mean particle diameter;
n.d. = not determined

III. Preparation of Aqueous Dispersions Containing UV Absorber Containing Polymers PD (PD. No. 11 to 19)

A reaction vessel fitted with stirrer was charged with deionized water and 0,6 g of sodium dodecylsulfate. The total amount of water was about 450 ml. A solution of the respective UV absorber in the monomers to be polymerized (monomer/dye solution) was added thereto over the course of 2 minutes. The amount and kind of UV absorber being used is given in table 2. The composition of the monomer solution was as follows: 5 g stearyl acrylate, 5 g butandiole diacralate, 95 g methyl methacrylate. The mixture was then stirred for a further 10 minutes. The resulting conventional dye containing monomer emulsions were then homogenized using ultrasound as follows to give an aqueous micro emulsion.

The ultrasound source used was a Branson Sonifier II 450. The macroemulsion was sonicated with stirring for 5 minutes at the setting duty-cycle 25%, output control 10, and for 10 minutes at the setting duty cycle 100% and output control 10. The size of the monomer droplets (volume average) in the obtained monomer emulsion was below 400 nm.

2. Polymerization of the Mini-emulsions

The resulting mini-emulsion was introduced in a polymerization vessel and heated to 80° C. The initiator solution was added in one portion (1 g sodium peroxodisulfate in 38 ml of water or 0,3 g $H_2O_2$ as 35% strength aqueous solution and 0,3 g ascorbic acid as aqueous solution for PD 19) the mixture was left to post-react for 3,5 h at 80 to 85° C., was then cooled to 25° C. and filtered over 75 µm sieve to determine the amount of coagulum. This gave an approxi-

TABLE 2

| | UV absorber | | LD [1)] | | viscosity |
|---|---|---|---|---|---|
| PD | type | %[2)] | [%] | pH | [mPas] |
| 11 | UV2 | 5 | 88, 1 | 2, 1 | 3, 4 |
| 12 | UV2 | 20 | 81, 0 | 2, 2 | 3, 7 |
| 13 | UV5 | 20 | 82, 0 | 2, 2 | 3, 7 |
| 14 | UV1 | 20 | 80, 7 | 2, 2 | 3, 7 |
| 15 | UV3 | 20 | 82, 3 | 2, 0 | 3, 7 |
| 16 | UV4 | 20 | 84, 0 | 2, 6 | 3, 7 |
| 17 | UV1 | 30 | 77, 4 | 2, 2 | 3, 7 |
| 18 | UV1 | 40 | 76, 3 | 2, 3 | 3, 7 |
| 19 | UV5 | 20 | 79, 4 | 2, 6 | 3, 9 |

[1)] light transmittance
[2)] % by weight, based on polymer

Measurement of Sun Protection Factor SPF

Sun protection factor was determined by means of on SPF-analyzer on samples containing 3% by weigth of an UV absorber.

sample 1: 3 g of UV absorber UV1 and 1 g of Cremophor RH60 in 96 g of water comparison sample 2: 3 g of UV absorber UV5 and 1 g of Cremophor RH60 in 96 g of water comparison sample 3: 15 g of polymer PD14 in 85 g of water (corresponding 3% UV1)

sample 4: 15 g of polymer PD13 in 85 g of water (corresponding 3% UV5)

sample 5: 15 g of polymer PD14 in 85 g of butylene glycol (corresponding 3% UV1)

sample 6: 15 g of polymer PD13 in 85 g of butylene glycol (corresponding 3% UV5)

The results of the measurements are given in table 3:

TABLE 3

SPF values

| sample | UV absorber | SPF value |
|---|---|---|
| 1 | UV1 | 9, 1 |
| 2 | UV2 | 6, 4 |
| 3 | UV1 | 9, 0 |
| 4 | UV2 | 9, 1 |
| 5 | UV1 | 10, 3 |
| 6 | UV2 | 10, 7 |

Formulations of polymers PD in cosmetic care compositions are described below by way of examples. All data is in grams. The quantitative data for the aqueous dispersions of the dye-containing polymer PD is based on the polymer proportion.

Nail Varnish Formulations (Formulation 1 to 3)

Formulation 1

26.3 nitrocellulose 4.9 copolymer of polyoxyisobutylene and methyleneurea 7.8 copolymer of butyl acrylate and vinyl isobutyl ether, 50% by weight in ethyl acetate (Acronal® 700 L 50% BASF)

4.9 methoxypropyl acetate 53.5 butyl acetate 2.6 polymer PD as powder

Formulation 2

16.0 nitrocellulose 4.0 toluenesulfonamide/formaldehyde resin 5.0 dibutyl phthalate 10.0 butyl acetate 10.0 ethyl acetate 10.0 ethanol 40.0 toluene 5.0 polymer PD as powder The constituents, with the exception of the aqueous dispersion of PD, are dissolved. The dye-containing polymer PD is then stirred in as aqueous dispersion, and the mixture is then homogenized.

Aqueous Nail Varnish: (Formulations 3 to 4)

Formulation 3

27.2 aqueous polyurethane dispersion 13.8 acrylic acid/styrene copolymer 0.08 polyacrylic acid thickener 0.5 butyl glycol acetate 2.4 polymerisat PD as aqueous dispersion water ad 100

The polyurethane is initially introduced as a finely disperse aqueous dispersion. The acrylic acid/styrene copolymer is added as aqueous dispersion with stirring. The acrylate thickener is then added with stirring. The mixture is further stirred until the material is of high viscosity. Finally, the aqueous dispersion of PD is stirred in.

Formulation 4

As Formulation 3, but using 0.4 g Acid Blue 74 Aluminium Lake and 2.0 g polymer PD as aqueous dispersion.

Mascara

Formulation 5

14.0 demin. water 0.2 antioxidant (Oxynex 2004 from E. Merck, Darmstadt)

2.5 polyoxyethylene/polyoxypropylene block copolymer (Poloxamer 407 from BASF Aktiengesellschaft)

3.5 polyvinylpyrrolidone 11.0 ethanol 0.7 triethanolamine 0.52 polyacrylic acid (CTFA: Carbomer)

57.58 demin. water 10.0 polymer PD as aqueous dispersion

The polyacrylic acid is left to swell in water, and then the clearly dissolved residual constituents are incorporated to give a gel. The aqueous dispersion of PD is then incorporated.

Eyelash Make-up

Formulation 6

80.8 castor oil 6.0 capryloc/capric triglyceride 0.2 antioxidant (Oxynex 2004 from E. Merck, Darmstadt)

2.0 trihydroxystearin 0.3 polyvinylpyrrolidone 2.0 sorbitan oleate 8.7 polymer PD as powder The fatty constituents are dissolved in one another. The polyvinylpyrrolidone is then stirred in. The pulverulent polymer PD is then mixed in.

Cream Mascara

Formulation 7

75.0 petroleum distillate 8.3 quaternium-18 hectorite 2.5 propylene carbonate 11.5 aqueous dispersion of PD 1.0 ultramarine 1.7 vinylpyrrolidone/vinyl acetate copolymer The components of the fatty phase are processed by means of strong shear forces to give a gel. The aqueous dispersion of the dye-containing polymer PD and the vinylpyrrolidone/vinyl acetate copolymer is then incorporated and homogenized.

Kohl Pencil-cosmetic Pencil

Formulation 8

34.3 hydroxylated lanolin 17.10 hydrogenated cocoglyceride 2.9 lanolin 28.6 glyceryl stearate 17.1 polymerisat PD as powder The fatty components are melted at 80° C. The pulverulent polymer PD is then mixed in, optionally perfumed, and molded by casting or extrudation to give leads for cosmetic pencils.

Eyeliner Pencil

Formulation 9

30.0 cyclomethicone 6.7 lanolin oil 8.0 carnauba wax 3.3 beeswax 22.7 paraffin oil 2.7 cetyl alcohol 20.0 polymer PD as powder 5.6 Pigment Blue 15

1.0 iron oxide pigment

Eyebrow Pencil
  Formulation 10
    78.0 Cutina LM (lipstick material from Henkel KGaA, Düsseldorf)
    12.0 ozokerite
    9.0 polymer PD as powder
    1.0 iron oxide pigment
Eye Shadows
  Formulation 11
    20 talc
    10 potato starch
    5 magnesium stearate
    45 polymer PD as powder
    5 ultramarine (Sicomet Blue P 77007)
    15 eye shadow binder
Eye Shadow Binder
    35 lanolin
    30 isopropyl stearate
    30 paraffin oil
    3 perfume oil
    1 carnauba wax
    1 propylparaben
  The eye shadow constituents are mixed homogeneously, and the pulverulent polymer PD and the color pigment (ultramarine) are stirred in. The binder constituents are melted at 70° C. The eye shadow constituents are sprayed together with the molten and well-mixed binder. The mixture is then compressed at a pressing force of 40 to 60 bar. This gives an eye shadow powder with a soft feel on the skin and a unique color effect.
  Formulation 12
    As previous formulation, but using 50 g of powder of PD instead of the ultramarine/PD mixture.
Eye Shadow in Stick Form
  Formulation 13
    15.0 triglyceride of a $C_{18-36}$-acid
    5.0 glyceryl behenate
    35.0 mineral oil
    15.0 mineral oil (and) lanolin alcohol
    0.2 perfume oil
    0.8 polyvinylpyrrolidone
    1.5 talc
    27.5 polymer PD as powder
  The fatty components are melted at 80° C., and the pulverulent polymer PD is mixed in. The mixture is then perfumed and shaped by casting or extrudation to give lead for cosmetic pencils.
Eye Shadow Pencil
  Formulation 14
    6.0 beeswax
    5.0 carnauba wax
    10.0 Candelilla wax
    34.0 hexyl laurate
    20.0 castor oil
    20.0 polymer PD as powder
    4.0 chromium oxide green pigment
    1.0 perfume oil
  Eye shadow pencils from the two above formulations can also be formulated with mixtures of color pigments and pulverulent polymers PD instead of the pure pulverulent polymer PF.

Cream Blusher (Formulations 15 and 16)
  Formulation 15
    5.5 candelilla wax
    8.5 beeswax
    3.0 cetyl palmitate
    8.5 paraffin oil
    43.0 cetearyl octanoate
    3.0 hydrogenated coconut fatty acid glyceride
    11.0 vaseline
    14.5 talc
    3.0 polymer PD as powder
  The constituents of the basic material are heated to about 80° C. and mixed well. The pulverulent polymer PD is then incorporated into the basic mixture.
  Formulation 16
    As Formulation 17, but instead of the pure powder PD, 0.5 g of Pigment Red 57:1 and 2.5 g of powder PD are incorporated instead of the pure powder PD.
Loose Powder Blusher (Formulations 17 to 19)
  Formulation 17
    77.0 talc
    10.0 magnesium stearate
    2.0 calcium carbonate
    0.5 vaseline
    0.5 paraffin oil
    10.0 polymer PD as powder
  The dry powder constituents are homogeneously mixed and mixed with the molten and well-mixed fatty constituents.
  Formulation 18
    As Formulation 17, although for a more intense red coloration, the pure pulverulent polymer PD can be replaced by a mixture of 1 to 2 g of red pigment, e.g. Pigment Red 172 Aluminium Lake and 8 to 9 g of pulverulent PD.
  Formulation 19
    As Formulation 18, but using 9.5 g of pulverulent polymer PD and 0.5 g of iron oxide pigment.
W/O Type Foundation
  Formulation 20
    5.5 hydrogenated castor oil, ethoxylated with 7 EO units
    7.0 cetearyl octanoate
    4.5 isopropyl myristate
    14.0 paraffin oil
    0.3 magnesium stearate
    0.3 aluminum stearate
    2.0 PEG-45/dodecyl glycol copolymer
    0.2 propylparaben
    5.0 propylene glycol
    0.6 magnesium sulfate
    0.1 paraben
    50.8 water
    0.2 perfume oil
    0.5 vitamin E acetate
    9.0 aqueous dispersion of PD (calculated as solid)
  The constituents of the fatty phase and of the water phase are heated separately at about 75° C., and the water phase is then slowly incorporated into the fatty phase with stirring. Following homogenization, the mixture is cooled to 40° C. with stirring, perfume oil and active ingredients are added, and the mixture is homogenized again. The aqueous dispersion of PD is then stirred in.

Formulation 21

As Formulation 20, but using 8 g of polymer PD, 0.5 g of iron oxide pigment and 0.5 g of titanium dioxide pigment.

O/W Type Foundation

Formulation 22

1.7 glyceryl stearate
1.7 cetyl alcohol
1.7 ceteareth-6, stearyl alcohol
1.7 ceteareth-25
5.2 caprylic/caprin triglyceride
0.2 methyldibromoglutaronitrile (and/or) phenoxyethanol
0.3 imidazolidinylurea
4.3 propylene glycol
69.0 demineralized water
0.2 perfume oil
14.0 polymer PD as aqueous dispersion The constituents of the fatty phase and of the water phase are heated separately to about 75° C. The water phase, together with the aqueous dispersion of PD, is then slowly incorporated into the fatty phase with stirring. The mixture is homogenized and cooled with stirring to 40° C., perfume oil is added as desired, and the mixture is homogenized again.

Formulation 23

As previous formulation, but using 12% of aqueous dispersion of PD, 1.5% of iron oxides and 0.5% of titanium dioxide.

Stage Make-up

Formulation 24

75.0 petroleum distillate
8.3 quaternium-18 hectorite
2.5 propylene carbonate
1.7 polyvinylpyrrolidone/vinyl acetate copolymer
12.5 polymer PD as powder

[The Spacing went Haywire here, Hopefully when Converted Back will Right Itself!]

The constituents are subjected to strong shear forces to prepare a gel. The copolymer and pulverulent polymer PD are incorporated. The mixture is then homogenized.

Formulation 25

As previous formulation 24, but using 11 g of polymer PD and 1.5 g of conventional color pigment, e.g. Pigment Blue 15.

Formulation 26

67.5 mineral oil
20.0 beeswax
10.0 ceresin wax
2.5 polymer PD as powder

Fatty components are melted and processed with pulverulent polymer PD to give a homogeneous paste.

Grease Make-up for the Stage in Stick Form

Formulation 27

22.0 ceresin wax
18.0 beeswax
44.0 mineral oil
5.0 turpentine
1.0 perfume oil
8.0 polymer PD as powder
2.0 iron hexacyanoferrate The fatty components are melted at 80° C., and the pulverulent polymer PD is mixed in. The composition is then perfumed and molded by casting or extrudation to give leads for cosmetic pencils.

Lipstick (Formulations 28 to 31)

Formulation 28

3.0 carnauba wax
3.5 candelilla wax
2.0 beeswax
7.0 microcrystalline wax
1,5 cetyl palmitate
5.0 vaseline
3.5 lanolin wax
2.0 lanolin
9.0 cetearyl octanoate
0.2 bisabolol
0.5 tocopherol
2.0 tocopheryl acetate
3.5 hydrogenated coconut fatty acid glyceride
42.3 castor oil
15.0 polymer PD as powder The constituents of the fatty composition are melted. The pulverulent polymer PD is then incorporated into the basic composition, and the homogeneous melt is poured into casting molds preheated to 60° C. The castings are removed from the molds while cold and, after warming to room temperature, are briefly flamed.

Formulation 29

14.0 oleyl alcohol
10.0 castor oil
6.0 diisopropyl adipate
5.0 stearamide MEA
10.0 polymer PD as powder
1.0 iron oxide pigment
9.0 stearyl heptanoate
7.0 isopropyl lanolate
8.0 carnauba wax
10.0 beeswax
5.0 cetyl alcohol
5.0 ozokerite
3.0 microcrystalline wax
2.0 polyethylene
2.0 petrolatum
2.0 mineral oil
1.0 perfume oil Formulation 30

10.0 hydroxyoctancosanyl hydroxystearate
9.0 candelilla wax
25.0 castor oil
7.9 isopropyl myristate
5.0 sorbitan trioleate
3.0 hydroxylated lanolin
6.0 butylene glycol
0.1 propylparaben
1.0 perfume oil
3.0 ultramarine
30.0 polymer PD as powder Formulation 31

40.0 casstor oil
10.0 mineral oil
9.0 hydrogenated castor oil
5.0 of cocoa butter 10.0 carnauba wax
5. Stearyl heptanoate
5.0 beeswax
10.0 lanolin
5.0 polymer PD as powder
1.0 perfume oil Hair Gel Formulations (Formulations 32 to 34)
Formulation 32
59.8 water
0.5 polyacrylic acid (CTFA: Carbomer)
1.2 triethanolamine
29.9 glycerol
2.0 propylene glycol
2.3 dimethicone copolyol
0. imidazolidinylurea
4.0 polymer PD as aqueous dispersion
Formulation 33
0.7 polyacrylic acid (CTFA: Carbomer)
92.1 water
0.7 hydrogenated castor oil, ethoxylated with 40 EO units
0.2 perfume oil
0.3 imidazolidinylurea
1.0 panthenol
3.0 polyvinylpyrrolidone
1.0 triethanolamine
1.0 polymer PD as aqueous dispersion
Formulation 34 (Styling Gel):
0.5 polyacrylic acid (CTFA: Carbomer)
74.7 water
15.0 ethanol
0.2 hydroxyethylcetyldimonium phosphate
6.0 polyvinylpyrrolidone
0.3 imidazolidinylurea
0.8 tetrahydroxypropylethylenediamine
2.5 polymer PD as aqueous dispersion Hair Sprays (Formulations 35 to 37)
Formulation 35
3.0 polyvinylpyrrolidone
4.0 vinylpyrrolidone/vinyl acetate copolymer
0.7 rosin acrylate
44.3 ethanol
3.0 polymer PD as aqueous dispersion
45.0 propane/butane The components, with the exception of the aqueous dispersion of the polymer PD, are dissolved. The aqueous dispersion of PD is then stirred in. Prior to containerizing, add a few glass beads.

Formulation 36
1.5 acrylic acid/acrylamide copolymer
0.11 aminomethylpropanol
0.02 cyclomethicone
6.0 water
3.0 polymer PD as aqueous dispersion
60.0 dimethyl ether
29.37 ethanol Formulation 37
The formulation corresponds to Formulation 36, but 2 g of the aqueous dispersion of PD and 1 g of Pigment Blue 15 are incorporated.

Hair Mascara (Formulations 38 to 40)
Formulation 38
15.0 mixture of beeswax, carnauba (Copernicia cerifera) wax, stearic acid, ceteareth-25, PEG-2 stearate SE, mineral oil, hydrogenated coconut oil and cetyl alcohol (Base RW 135, Wacker)
1.5 dimethicone
0.5 preservative
42.1 water
0.45 triethanolamine
0.45 xanthan, hectorite and cellulose gum
30.0 acrylic acid copolymer
10.0 polymer PD as aqueous dispersion Formulation 39
As Formulation 38, but using 8 g of polymer PD and 2 g of Pigment Blue 15.

Formulation 40
14.0 demin. water
0.3 imidazolidinylurea
2.5 Poloxamer 407
3.5 polyvinylpyrrolidone
11.0 ethanol
0.7 triethanolamine
0.52 carbomer
57.48 demineralized water
1.0 iron oxide pigment
9.0 polymer PD as aqueous dispersion The components are formulated as gel, the color pigment and the aqueous dispersion of PD being fed in last.

Sunblock Stick
Formulation 41
4.0 carnauba wax
4.0 candelilla wax
4.0 beeswax
9.0 microcrystalline wax
1.0 cetyl palmitate
10.0 lanolin wax
5.0 ethoxylated lanolin oil, 75 ethylene oxide units
5.0 cetearyl octanoate
38.1 caprylic/capric triglyceride
0.2 perfume oil
2.0 titanium dioxide
0.5 tocopherol
2.0 tocopheryl acetate
0.2 bisabolol
15.0 polymer PD as powder The constituents of the fatty composition are melted. The titanium dioxide is then stirred in. At 65° C., the active ingredients and the pulverulent polymer PD are incorporated into the basic composition. The homogeneous melt is poured into casting molds preheated to 60° C.

Colored Soap:
Formulation 42
92.9 soap flakes
2.0 polyquaternium-16
0.1 bisabolol
0.4 tetrasodium EDTA
2.0 perfume oil
1.0 PEG-6
1.6 water 0.5 g of an aqueous dispersion of PD into 100 g of the basic soap composition comprising said constituents.

Formulation 43

4.2 sodium hydroxide 5.6 water 22.6 propylene glycol 5.2 cocoamide DEA 10.4 cocamine oxide 4.2 sodium lauryl sulfate 7.3 myristic acid 16.6 stearic acid 5.2 tocopheryl acetate 18.7 glycerol The ingredients are mixed and, at 85° C., are melted to give a clear melt. 100 parts of the basic soap composition are mixed with 3 parts of an aqueous dispersion of the polymer PD, and the resulting composition is poured into molds while still hot.

Color-imparting Hair Foam (Formulations 44 and 45)

Formulation 44

2.0 cocotrimonium methosulfate 0.2 perfume oil 7.0 polyquaternium-64

2.0 polyquaternium-11

0.2 cetheareth 25

0.5 panthenol 0.05 benzophenone-4

0.2 mixture of amodimethicon, tallow trimonium chloride and nonoxynol 10

0.2 hydroxyethylcellulose 15.0 ethanol 1.5 polymer PD as aqueous dispersion 10.0 propane/butane water ad 100 g The components are mixed and containerized together with the propellant.

Formulation 45

2.0 cocotrimonium methosulfate 0.2 perfume oil 6.7 acrylic acid copolymer 0.6 aminomethylpropanol 2.5 polyvinylcaprolactam 0.2 cetheareth 25

0.2 panthenol 0.1 PEG-25 PABA 0.2 hydroxyethylcellulose 15.0 ethanol 1.0 polymer PD as aqueous dispersion 10.0 propane/butane water ad 100 g Colored Hair Shampoo Formulation 46

40.0 sodium lauryl sulfate 10.0 cocoamidopropylbetaine q.s. perfume oil 3.0 polyquaternium-44 q.s. preservative 0.5 sodium chloride 1.5 polymer PD as aqueous dispersion water ad 100 g Sun Protection Creme Formulation 47

1,5 ceteareth 6

1,0 cetanol 3,0 cetearyloctanoate 5,0 polymer PD 18 as a powder 2,0 butylmethoxydibenzoylmethane 6,0 isopropylstearate 1,0 glycerylstearate 2,0 stearic acid 3,0 polyethylenglykole 300

0,3 carbomer 0,6 tetrahydroxypropylethylendiamine 0,1 disodium-EDTA 0,1 butylparaben 0,2 methylparaben 4,2 water

We claim:

1. The method of making a colored cosmetic composition, said method being characterised by incorporating at least one finely divided, dye-containing polymer PD in the form of an aqueous polymer dispersion or a polymer powder obtainable therefrom, the polymer matrix of which comprises at least one organic dye D in homogeneously dispersed form, as color-imparting constituent into a non-colored cosmetic base composition.

2. The method of claim 1, wherein the polymer particles of the dye-containing polymer PD have a particle size of ≦500 nm.

3. The method of claim 1, wherein the dye-containing polymer PD comprises 0.5 to 50% by weight, based on the weight of the polymer matrix, of the organic dye D.

4. The method of claim 3, wherein the dye-containing polymer PD comprises from 5 to 50% by weight, based on the weight of the polymer matrix, of the organic dye D.

5. The method of claim 1, wherein the monomers M comprise:

50 to 99.9% by weight of at least one monoethylenically unsaturated monomer A having a solubility in water in the range from 0.01 to 60 g/l at 25° C., 0.1 to 30% by weight of at least one crosslinking monomer B, 0 to 20% by weight of one or more monoethylenically unsaturated monomers C having a solubility in water of <0.01 g/l at 25° C., and 0 to 30% by weight of one or more monoethylenically unsaturated monomers D having a solubility in water of >60 g/l at 25° C., where the quantitative proportions of monomers A, B, C and D add up to 100% by weight.

6. The method of claim 1, wherein the cosmetic composition is in the form of a composition for treating facial skin, in the form of a composition for treating eyebrows and eyelashes, in the form of a nail varnish, in the form of a hair-treatment composition, in the form of a soap or in the form of a sunscreen formulation.

7. The method of claim 1, wherein the cosmetic composition is in the form of a sunscreen formulation which contains as a color-imparting constituent at least on UV absorber containing polymer PD.

8. The method of claim 7, wherein the polymer PD contains at least one UV absorber in an amount of from 5 to 30% by weight, based on the polymer matrix.

* * * * *